United States Patent
Coe et al.

(10) Patent No.: US 10,327,751 B2
(45) Date of Patent: Jun. 25, 2019

(54) METHODS AND APPARATUS FOR REDUCING THE RISK OF SURGICAL SITE INFECTIONS

(71) Applicant: Prescient Surgical, Inc., Mountain View, CA (US)

(72) Inventors: Jonathan Coe, Mountain View, CA (US); Insoo Suh, San Francisco, CA (US); Jeremy Koehler, Menlo Park, CA (US)

(73) Assignee: Prescient Surgical, Inc., San Carlos, CA (US)

( * ) Notice: Subject to any disclaimer, the term of this patent is extended or adjusted under 35 U.S.C. 154(b) by 199 days.

(21) Appl. No.: 14/220,928

(22) Filed: Mar. 20, 2014

(65) Prior Publication Data
US 2014/0343366 A1 Nov. 20, 2014

Related U.S. Application Data

(60) Provisional application No. 61/803,461, filed on Mar. 20, 2013.

(51) Int. Cl.
*A61B 17/02* (2006.01)
*A61B 90/30* (2016.01)
(Continued)

(52) U.S. Cl.
CPC ...... *A61B 17/0293* (2013.01); *A61B 17/3423* (2013.01); *A61B 90/30* (2016.02);
(Continued)

(58) Field of Classification Search
CPC .. A61M 1/0058; A61M 1/006; A61M 1/0084; A61M 1/0023; A61M 27/00; A61M 3/0279; A61G 13/102; A61G 13/108; A61F 13/00068; A61F 2013/00536; A61F 2013/0054; A61F 7/034; A61N 2217/005; A61N 2217/007; A61B 17/0293; A61B 17/3423; A61B 17/3462; A61B 2017/3492; A61B 2217/005; A61B 2217/007; A61B 2217/00; A61B 2017/00557; A61B 2017/3445; A61B 2017/3466; A61B 2017/0287; A61B 17/0218; A61B 18/06; A61B 2017/3484; A61B 2017/3429
(Continued)

(56) References Cited

U.S. PATENT DOCUMENTS 754,893 A 3/1904 Robertson
1,157,202 A 10/1915 Uri et al.
(Continued)

OTHER PUBLICATIONS

U.S. Appl. No. 14/209,393, filed Mar. 13, 2014, Koehler et al.
International search report and written opinion dated Sep. 5, 2014 for PCT/US2014/031366.

*Primary Examiner* — Diane D Yabut
*Assistant Examiner* — Majid Jamialahmadi
(74) *Attorney, Agent, or Firm* — Wilson Sonsini Goodrich & Rosati

(57) ABSTRACT

A surgical access system that facilitates access to a surgical site through an incision in the patient's body includes a surgical retractor and a fluid delivery or fluid evacuation device. The fluid delivery or fluid evacuation device is coupled to the surgical retractor and is adapted to deliver fluid to the surgical site or evacuate fluid from the surgical site.

52 Claims, 20 Drawing Sheets

(51) Int. Cl.
*A61B 17/34* (2006.01)
*A61M 1/00* (2006.01)
*A61M 3/02* (2006.01)
*A61F 7/03* (2006.01)

(52) U.S. Cl.
CPC ........ *A61M 1/0084* (2013.01); *A61M 3/0279* (2013.01); *A61B 17/3462* (2013.01); *A61B 2017/0287* (2013.01); *A61B 2017/3484* (2013.01); *A61B 2017/3492* (2013.01); *A61B 2217/005* (2013.01); *A61B 2217/007* (2013.01); *A61F 7/034* (2013.01)

(58) Field of Classification Search
USPC ..... 600/205–208; 604/540, 541, 26, 103.01; 222/187, 175, 152, 192; 224/148.1, 148.2
See application file for complete search history.

(56) References Cited

U.S. PATENT DOCUMENTS

| | | |
|---|---|---|
| 1,810,466 A | 6/1931 | Deutsch |
| 2,305,289 A | 12/1942 | Coburg |
| 2,812,758 A | 11/1957 | Blumenschein |
| 3,111,943 A | 11/1963 | Orndorff |
| 3,332,417 A | 7/1967 | Blanford et al. |
| 3,347,226 A | 10/1967 | Harrower |
| 3,347,227 A | 10/1967 | Harrower |
| 3,347,277 A | 10/1967 | Gwinn, Jr. |
| 3,397,692 A | 8/1968 | Creager, Jr. et al. |
| 3,402,710 A | 9/1968 | Paleschuck |
| 3,416,520 A | 12/1968 | Creager, Jr. |
| 4,024,872 A | 5/1977 | Muldoon |
| 4,188,945 A | 2/1980 | Wenander |
| 4,553,537 A | 11/1985 | Rosenberg |
| 4,777,943 A | 10/1988 | Chvapil |
| 4,889,107 A | 12/1989 | Kaufman |
| 4,942,700 A | 7/1990 | Hoberman et al. |
| 4,984,564 A | 1/1991 | Yuen |
| 5,024,031 A | 6/1991 | Hoberman et al. |
| 5,105,983 A | 4/1992 | Sancoff et al. |
| 5,146,916 A | 9/1992 | Catalani |
| 5,159,921 A | 11/1992 | Hoover |
| 5,263,922 A | 11/1993 | Sova et al. |
| 5,284,481 A | 2/1994 | Soika et al. |
| 5,352,201 A | 10/1994 | Jemmott |
| 5,358,494 A | 10/1994 | Svedman |
| 5,364,356 A | 11/1994 | Hoefling |
| 5,366,478 A | 11/1994 | Brinkerhoff et al. |
| 5,437,683 A | 8/1995 | Neumann et al. |
| 5,522,791 A | 6/1996 | Leyva |
| 5,524,464 A | 6/1996 | Asada et al. |
| 5,524,644 A | 6/1996 | Crook |
| 5,616,121 A | 4/1997 | McKay |
| 5,632,284 A | 5/1997 | Graether |
| 5,649,550 A | 7/1997 | Crook |
| 5,741,298 A | 4/1998 | MacLeod |
| 5,810,721 A | 9/1998 | Mueller et al. |
| 5,832,925 A | 11/1998 | Rothrum |
| 5,842,971 A | 12/1998 | Yoon |
| 5,853,395 A | 12/1998 | Crook et al. |
| 5,871,474 A | 2/1999 | Hermann et al. |
| 5,899,208 A | 5/1999 | Bonadio |
| 5,902,266 A | 5/1999 | Leone et al. |
| 5,906,577 A | 5/1999 | Beane et al. |
| 5,945,932 A | 8/1999 | Smith et al. |
| 5,947,922 A | 9/1999 | MacLeod |
| 5,951,588 A | 9/1999 | Moenning |
| 5,964,781 A | 10/1999 | Mollenauer et al. |
| 6,010,494 A | 1/2000 | Schaefer et al. |
| 6,033,426 A | 3/2000 | Kaji |
| 6,045,535 A | 4/2000 | Ben Nun |
| 6,048,309 A | 4/2000 | Flom et al. |
| 6,077,288 A | 6/2000 | Shimomura et al. |
| 6,086,603 A * | 7/2000 | Termin ............... A61B 17/3421 604/164.01 |
| 6,090,043 A | 7/2000 | Austin et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,162,172 A | 12/2000 | Cosgrove et al. |
| 6,254,533 B1 | 7/2001 | Fadem et al. |
| 6,254,534 B1 | 7/2001 | Butler et al. |
| 6,382,211 B1 | 5/2002 | Crook |
| 6,383,162 B1 | 5/2002 | Sugarbaker |
| 6,440,063 B1 | 8/2002 | Beane et al. |
| 6,450,983 B1 | 9/2002 | Rambo |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,695,824 B2 | 2/2004 | Howard et al. |
| 6,723,044 B2 | 4/2004 | Pulford et al. |
| 6,814,078 B2 | 11/2004 | Crook |
| 6,814,700 B1 | 11/2004 | Mueller et al. |
| 6,846,287 B2 | 1/2005 | Bonadio et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 7,008,377 B2 | 3/2006 | Beane et al. |
| 7,033,319 B2 | 4/2006 | Pulford et al. |
| 7,052,454 B2 | 5/2006 | Taylor |
| 7,081,089 B2 | 7/2006 | Bonadio et al. |
| 7,163,510 B2 | 1/2007 | Kahle et al. |
| 7,195,590 B2 | 3/2007 | Butler et al. |
| 7,214,185 B1 * | 5/2007 | Rosney ............... A61B 17/3423 600/208 |
| 7,235,062 B2 | 6/2007 | Brustad |
| 7,238,154 B2 | 7/2007 | Ewers et al. |
| 7,297,106 B2 | 11/2007 | Yamada et al. |
| 7,300,399 B2 | 11/2007 | Bonadio et al. |
| 7,377,898 B2 | 5/2008 | Ewers et al. |
| 7,393,322 B2 | 7/2008 | Wenchell |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,758,500 B2 | 7/2010 | Boyd et al. |
| 7,815,567 B2 | 10/2010 | Albrecht et al. |
| 7,867,164 B2 | 1/2011 | Butler et al. |
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,909,760 B2 | 3/2011 | Albrecht et al. |
| 7,909,761 B2 | 3/2011 | Banchieri et al. |
| 7,913,697 B2 | 3/2011 | Nguyen et al. |
| 7,928,281 B2 | 4/2011 | Augustine et al. |
| 7,951,076 B2 | 5/2011 | Hart et al. |
| 7,967,748 B2 | 6/2011 | Kistler et al. |
| 7,998,068 B2 | 8/2011 | Bonadio et al. |
| 8,012,088 B2 | 9/2011 | Butler et al. |
| 8,016,755 B2 | 9/2011 | Ewers et al. |
| 8,021,296 B2 | 9/2011 | Bonadio et al. |
| 8,070,676 B2 | 12/2011 | Ewers et al. |
| 8,105,234 B2 | 1/2012 | Ewers et al. |
| 8,109,873 B2 | 2/2012 | Albrecht et al. |
| 8,142,354 B1 | 3/2012 | Larson et al. |
| 8,226,552 B2 | 7/2012 | Albrecht et al. |
| 8,227,657 B2 * | 7/2012 | Aali ............... A61F 15/008 128/888 |
| 8,241,260 B2 | 8/2012 | Livne et al. |
| 8,357,188 B2 | 1/2013 | Boynton et al. |
| 8,857,440 B2 | 10/2014 | Gundlapalli et al. |
| 9,220,837 B2 | 12/2015 | Pesach et al. |

(56) References Cited

U.S. PATENT DOCUMENTS

| | | |
|---|---|---|
| 9,402,973 B2 | 8/2016 | Phillips et al. |
| 2002/0002324 A1 | 1/2002 | McManus |
| 2003/0187376 A1 | 10/2003 | Rambo |
| 2003/0192553 A1 | 10/2003 | Rambo |
| 2004/0154624 A1 | 8/2004 | Bonadio et al. |
| 2004/0267096 A1 | 12/2004 | Caldwell et al. |
| 2005/0020884 A1 | 1/2005 | Hart et al. |
| 2005/0119613 A1 | 6/2005 | Moenning et al. |
| 2005/0148823 A1 | 7/2005 | Vaugh et al. |
| 2005/0155611 A1 | 7/2005 | Vaugh et al. |
| 2005/0261720 A1 | 11/2005 | Caldwell et al. |
| 2005/0283050 A1 | 12/2005 | Gundlapalli et al. |
| 2006/0025749 A1 | 2/2006 | Moenning |
| 2006/0095020 A1 | 5/2006 | Casas et al. |
| 2006/0149306 A1 | 7/2006 | Hart et al. |
| 2006/0161050 A1 | 7/2006 | Butler et al. |
| 2006/0217596 A1 | 9/2006 | Williams |
| 2007/0259147 A1 | 11/2007 | Boudry et al. |
| 2008/0275408 A1 | 11/2008 | Boynton et al. |
| 2008/0294127 A1* | 11/2008 | Blott ................ A61M 1/0037 604/305 |
| 2010/0100043 A1 | 4/2010 | Racenet |
| 2010/0234794 A1* | 9/2010 | Weadock ............ A61G 13/108 604/20 |
| 2010/0280326 A1 | 11/2010 | Hess et al. |
| 2011/0034888 A1 | 2/2011 | Aali |
| 2011/0054260 A1* | 3/2011 | Albrecht ........... A61B 17/0218 600/208 |
| 2011/0137267 A1 | 6/2011 | Phillips et al. |
| 2011/0313383 A1* | 12/2011 | Hofstetter ............ A61F 13/00 604/372 |
| 2012/0209078 A1* | 8/2012 | Pribanic ......... A61B 17/3423 600/208 |
| 2013/0178709 A1* | 7/2013 | Suh ................ A61B 17/0293 600/205 |
| 2013/0178710 A1 | 7/2013 | Suh et al. |
| 2013/0184535 A1 | 7/2013 | Suh et al. |
| 2013/0194375 A1 | 8/2013 | Michrowski et al. |

* cited by examiner

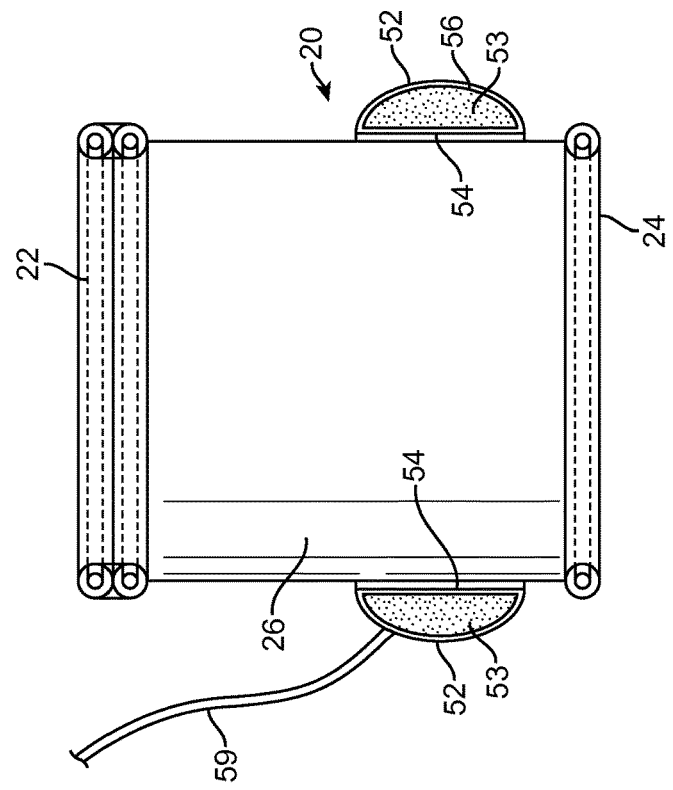
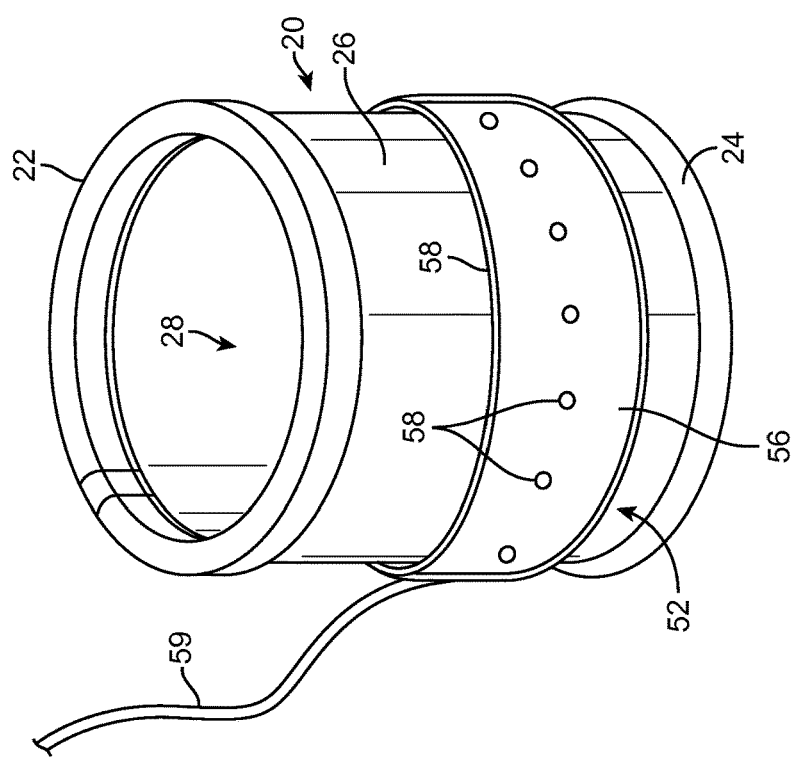
FIG. 8A
FIG. 8B

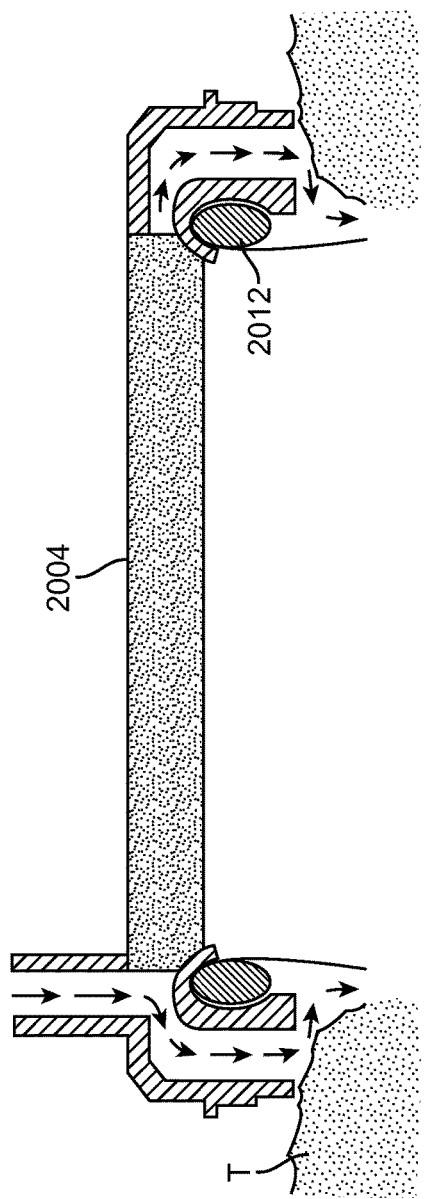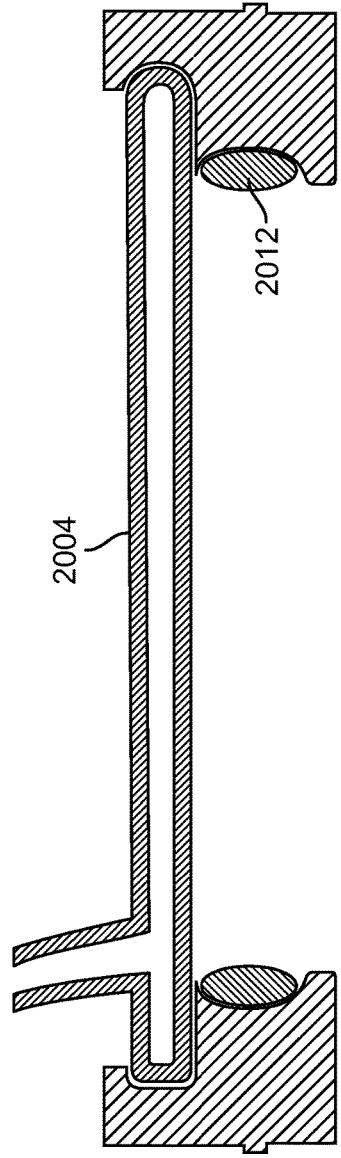

METHODS AND APPARATUS FOR REDUCING THE RISK OF SURGICAL SITE INFECTIONS

CROSS-REFERENCE

The present application is a non-provisional of, and claims the benefit of U.S. Provisional Patent Application No. 61/803,461 filed on Mar. 20, 2013; the entire contents of which are incorporated herein by reference.

The present application is related to U.S. patent application Ser. Nos. 13/736,904; 13/736,888; 13/736,875; and 14/209,393; the entire contents of which are incorporated herein by reference.

BACKGROUND OF THE INVENTION

1. Field of the Invention

The present application generally relates to medical devices, systems and methods, and more particularly relates to devices, methods and systems for reducing the risk of surgical site infections.

Formerly known as "wound infection," surgical site infection (SSI) is generally defined by the Centers for Disease Control and Prevention (CDC) as an infection in the area of the surgical incision that occurs within 30 days of an operation. The CDC further subdivides SSI into two groups. The first group includes superficial and deep "incisional" SSI (ISSI). The second group includes "organ/space" SSI. These two groups appear to be somewhat different phenomena with respect to etiology, physiology, pathogenesis, clinical presentation, and treatment. Of note, the term "wound infection," as currently used in the medical colloquium, refers to and is more compatible with ISSI, as opposed to organ/space SSI.

ISSI affects approximately 3-4% of the more than 30 million operations performed in the U.S. each year. Although the state of current medical care has minimized the mortality associated with ISSI, the morbidity and associated costs to the healthcare system remain significant. On average, ISSI extends the length of an inpatient hospital stay by 9 days, as well as introduces the added necessity and costs of outpatient wound management, which can reach upwards of 10,000-45,000 U.S. dollars per patient. Estimates of the aggregate annual burden to the U.S. healthcare system exceed five billion U.S. dollars.

The diagnosis of SSI is usually made by a physician and is usually based on the clinical finding of various signs and symptoms of infection at the incisional site, such as pain, tenderness, swelling, redness, warmth, and purulent drainage. Various ancillary tests, such as microbial cultures or radiographic exams (e.g., computed tomography scans), can aid in the diagnosis. The length of treatment can extend for weeks or even months.

Obese patients are particularly vulnerable to developing wound infections, with a two to three fold increased risk relative to the overall population. This is at least partially due to the poor vascularization of subcutaneous fat, reducing the delivery of prophylactic intravenous (IV) antibiotics to the incision site. Furthermore, subcutaneous fat is an excellent media for the incubation of bacterial infection. With increasing rates of obesity worldwide, this will only further compound the problem of ISSI.

Another risk factor for the development of ISSI is the type of surgical procedure performed. For example, colorectal surgeries are associated with a baseline infection rate of 15-20%. This is a result of the contaminated nature of the procedure, as fecal contents are often released into the operative field when colon, small bowel, or rectum is cut. Furthermore, colorectal surgery involves the manipulation and removal of large organs (e.g. the colon), and consequently, large incisions are often required to perform the procedures. ISSI risk is directly correlated with the size of surgical incision used to perform the case. These risks are further compounded when combined with other risk factors such as obesity. For example, the rates of wound infections in obese patients undergoing colorectal surgery increase to upwards of 33%, representing a major burden to the healthcare system in terms of the quality and cost of services.

Prior surgical instruments and methods have been developed with the aim of reducing wound infections, yet the scope of the problem has not been reduced. Some solutions have addressed the issue by implanting degradable sponges in the incision to combat the development of wound infections post-operatively. However, this approach led to increases in wound infection rates, as the immune system reacts poorly to the implant because the implant is a "foreign body."

Surgeons have previously irrigated the incision or wound margins with fluids such as saline and/or antibiotics, but the practice has proved to be disruptive to surgical progress, difficult to implement and standardize in surgical practices, and consumes valuable time, increasing patient risk and increasing operative costs.

Barrier wound protectors have also been employed to prevent the egress of bacteria into the incision, but this is merely a passive approach, and considering the barrier protection must be removed to complete the operation, the incision is inevitably exposed to the infectious contents contained within the surgical field. Additionally, wound protectors may be difficult to manipulate, especially when positioned in the surgical field. A further drawback is that the barrier can also trap bacteria onto the wound surface, allowing bacteria to proliferate in the wound space.

Considering the significant morbidity and cost associated with SSI, it is desirable to provide a way to reduce the occurrence of SSI that is superior to the limitations of currently available commercial devices.

In addition to the challenges mentioned previously, in select situations, a key aspect of surgery involves obtaining adequate surgical "exposure," or alternatively, adequate visualization and access to target anatomical landmarks and structures to be operated upon. To achieve proper exposure, surgeons can use a variety of surgical retractors generally configured to maximize the opening of the incision and create space within the operative region (e.g. chest, abdomen, orbit, neck, and groin) to facilitate the completion of the surgical procedure.

One surgical retractor used in abdominal surgery involves a top ring, bottom ring, and a flexible tubular sheath (also referred to as a pliable membrane) disposed between the top and bottom rings. In numerous embodiments, manipulation of the top ring in a variety of ways (e.g., by rolling the sheath around the top ring) is sometimes effective to shorten the sheath length and retract the edges of the incision. In many cases, such surgical retractors incorporate barrier wound protection, the potential disadvantages of which have already been described.

The drawbacks of surgical retractors described in currently available commercial devices are numerous. They can be difficult to use, requiring additional time and the manual application of forces that may be difficult for surgeons to apply in an operative setting. They may require more than one person to operate, decreasing focus on the operative field, increasing operative time and personnel costs. In addition, due to the unpredictable nature of a surgical operation, the initial incision size may not be ideal, thus requiring lengthening during the course of the procedure. Many commercially available surgical retractors do not allow for an increase in incision size with the device in situ. Moreover, currently available commercial surgical retractors may employ a design requiring a variety of sizes to accommodate the wide range of incision sizes encountered during surgery. As a result, hospitals may have to stock a range of device sizes, and often multiple devices are used in a single procedure as the size of the incision may be increased. Using multiple devices may result in increased healthcare costs, surgery duration, and infections.

As noted previously, it may be advantageous to incorporate the combined functions of fluid delivery and fluid removal into a retraction device configured to reduce the risk of surgical site infections. Proposed embodiments of such a device may provide fluidic functions that are generally disposed along or near a pliable membrane, and that are configured to provide barrier wound protection (preventing direct contamination of the wound edges) and retraction of the surgical wound to permit visualization and access to the surgical site. U.S. patent application Ser. Nos. 13/736,888 and 13/736,904 disclose further details about such a device, the entire contents of which are incorporated herein by reference. Methods of using such a device are also disclosed in U.S. patent application Ser. No. 13/736,785, the entire contents of which are incorporated herein by reference. Additional disclosure about various features which may be used in such a device are disclosed in U.S. patent application Ser. No. 14/209,393, the entire contents of which are incorporated herein by reference. While these embodiments are preferred due to their ability to accommodate a range of incision sizes, their ability to increase the size of the incision without removing the retraction device from the surgical field, and their speed of use, among other benefits, it may be beneficial to implement fluid delivery and optionally fluid evacuation with other commercially available retractors. One such exemplary commercial retractor includes a dual ring wound retractor design described in U.S. patent application Ser. Nos. 12/873,115, and 12/119,414; U.S. Pat. Nos. 5,524,464, 7,238,154, 6,254,533, 6,814,078, 6,382,211, 8,021,296, and 8,012,088, among others. Generally, these devices are comprised of a cylindrical sheath disposed between a top and bottom ring. Shortening of the cylindrical sheath is generally effective to retract the wound opening, thereby permitting completion of a surgical procedure therethrough. It may be beneficial to combine fluid delivery and optionally fluid evacuation features with these devices to provide the advantages previously discussed above.

Such devices may provide better treatment of SSI, and preferably are easier to use, optimize fluid management within the surgical wound, and reduce manufacturing costs and complexity. At least some of these objectives will be met by the embodiments disclosed below.

2. Description of the Background Art

The follow U.S. Patent Applications and U.S. Patents are relevant to surgical retractors: Ser. Nos. 12/873,115; 12/119, 414; U.S. Pat. Nos. 5,524,464; 7,238,154; 6,254,533; 6,814, 078; 6,382,211; 8,021,296; and 8,012,088.

SUMMARY OF THE INVENTION

The present invention generally relates to medical systems, devices and methods, and more particularly relates to methods and apparatus for the treatment of surgical site infection.

In a first aspect of the present invention, a surgical access system that is adapted to facilitate access to a surgical site through an incision in a patient's body comprises a surgical retractor and a first fluid delivery or fluid evacuation device. The first fluid delivery or fluid evacuation device is coupled with the surgical retractor, and is configured to deliver fluid or evacuate fluid from the surgical site.

The surgical retractor may comprise an upper retention member, a lower retention member, and a membrane disposed therebetween. The upper retention member may comprise an expandable and collapsible ring, and the lower retention member may comprise a resilient ring. The surgical retractor may comprise an upper ring and a lower ring, and a plurality of elongate flexible elements may be coupled to the rings. The plurality of elongate flexible elements may comprise a plurality of chain links.

The first fluid delivery or fluid evacuation device may comprise a plurality of elongate arms disposed around the retractor. The elongate arms may have a channel disposed therein for delivering the fluid or evacuating the fluid. The surgical retractor may comprise a pliable membrane formed into a cylinder or a frustoconical shape, and the plurality of elongate arms may be disposed around the pliable membrane. The plurality of elongate arms may comprise arcuate arms having a curvature that substantially conforms to a surface of the surgical retractor. A plurality of holes may be disposed in at least some of the plurality of elongate arms. The first fluid delivery or fluid evacuation device may be a fluid delivery device, and the holes may be configured to allow delivery of fluid from the fluid delivery device to the surgical site, or the first fluid delivery or fluid evacuation device may be a fluid evacuation device and the plurality of holes may be configured to allow delivery of a vacuum from the fluid evacuation device to the surgical site.

The first fluid delivery or fluid evacuation device may further comprise a fluid delivery or fluid removal tube fluidly coupled thereto and configured to deliver fluid from a fluid source to the device or configured to deliver a vacuum from a vacuum source to the device. The first fluid delivery or fluid evacuation device may comprise a dual layer membrane with a channel disposed therebetween, and the channel may be fluidly coupled with the fluid delivery or fluid removal tube. The first fluid delivery or fluid evacuation device may comprise a receptacle for receiving the surgical retractor, thereby reducing profile where the fluid delivery or fluid evacuation device engages the surgical retractor. In other embodiments, the surgical retractor may comprise a receptacle adjacent and upper portion of the retractor, and the receptacle may be configured to receive the first fluid delivery or fluid evacuation device. This reduces the profile where the fluid delivery or fluid evacuation device engages the surgical retractor. The first fluid delivery or fluid evacuation device may be configured to deliver fluid to the surgical site and may be configured to evacuate fluid from the surgical site. The first fluid delivery or fluid evacuation device may comprise a bracelet disposed around an outer surface of the surgical retractor. The bracelet may be a closed ring, or it may comprise an inner layer of material, an outer layer of material and a support member disposed therebetween. The support member may provide support to prevent collapse of the inner and outer layers toward one another. The bracelet may comprise an inner layer of material, an outer layer of material and a fluid dispersion member disposed therebetween and that may be configured to distribute the fluid about a perimeter of the bracelet.

The first fluid delivery or fluid evacuation device may comprise a plurality of elongate fingers disposed circumferentially around the surgical retractor, and the plurality of elongate fingers may extend into the surgical site. The first fluid delivery or fluid evacuation device may be discrete and releasably coupled with the surgical retractor. The first fluid delivery or fluid evacuation device may be integrally formed with the surgical retractor. The first fluid delivery or fluid evacuation device may comprise a permeable outer layer of material fixedly attached to the surgical retractor thereby forming a channel disposed therebetween, and fluid or vacuum may be delivered through the channel and through the permeable outer layer of material to the surgical site.

The system may further comprise an intermediate layer of material disposed in the channel. The intermediate layer of material may be configured to support the channel and help prevent collapse of the permeable outer layer of material and the surgical retractor toward one another. The intermediate layer may comprise foam.

The first fluid delivery or fluid evacuation device may be a fluid delivery device and a fluid may be stored in the fluid delivery device, and the fluid may be delivered to the surgical site without requiring fluid coupling between the fluid delivery device and an external fluid source. The fluid may be stored in an absorbable material coupled to the first fluid delivery device.

The first fluid delivery of fluid evacuation device may comprise a layer of absorbent material that holds the fluid and that may be configured to deliver the fluid to the surgical site. The first fluid delivery or fluid evacuation device may be a fluid evacuation device that comprises a second layer of absorbent material that is positioned to absorb excess fluid from the surgical site. The surgical site has a depth, and the layer of absorbent material may comprise an outer permeable surface having a height, and the height may substantially match the depth of the surgical site.

The first fluid delivery or fluid evacuation device may comprise an inner layer of material and an outer permeable layer of material, and the layers of material may be sealed to one another in a quilted pattern. The first fluid delivery or fluid evacuation device may be a fluid evacuation device that may comprise a gutter for collecting the fluid.

The system may further comprise a second fluid delivery or fluid evacuation device coupled with the surgical retractor. The second device may be configured to deliver fluid to the surgical site or configured to evacuate fluid from the surgical site. The first device may deliver fluid to the surgical site and the second device may deliver a vacuum to the surgical site to evacuate fluid from the surgical site. The second device may comprise a bracelet disposed around an outer surface of the surgical retractor. The system may further comprise the fluid, and the fluid may be saline or an antibiotic. The system may also comprise an exothermic reagent for generating heat and warming the surgical site.

The system may further comprise a circulating system for collecting the fluid from the surgical site and redelivering the fluid to the surgical site. The system may also comprise a sealing element disposed between a patient's skin and the surgical retractor or the first fluid delivery or fluid evacuation device. The sealing element may be configured to prevent leakage of the fluid from the surgical site. The system may also comprise a surgical access port that has a resilient access membrane biased to collapse into a relaxed configuration thereby substantially closing any punctures formed by a hand or surgical instrument passing through the resilient access membrane.

In another aspect of the present invention, a method for accessing a surgical site through an incision in a patient's body comprises providing a surgical retractor and a first fluid delivery or fluid evacuation device, inserting the retractor through the incision, and coupling the first fluid delivery or fluid evacuation device with the surgical retractor. The method also comprises retracting tissue in the surgical site with the surgical retractor, and delivering fluid to the surgical site from the first fluid delivery or evacuation device, or evacuating fluid from the surgical site to the first fluid evacuation device.

Coupling may comprise disposing a plurality of arms around an outer surface of the surgical retractor. Or coupling may comprise receiving the surgical retractor in a receptacle on the first fluid delivery or evacuation device thereby reducing overall profile where the surgical retractor and the first fluid delivery or evacuation device engage one another. Coupling may also comprise receiving the first fluid delivery or fluid evacuation device in a receptacle on the surgical retractor thereby reducing overall profile where the surgical retractor and the first fluid delivery or fluid evacuation device engages one another.

Retracting the tissue may comprise radially expanding or collapsing an expandable or collapsible upper retention ring coupled to the surgical retractor. A fluid delivery or a suction tube may be coupled to the first fluid delivery or fluid evacuation device. The fluid delivery tube or the suction tube may allow a fluid connection between the first fluid delivery or fluid evacuation device and a source of the fluid, or a source of vacuum. The first fluid delivery or fluid evacuation device is a fluid delivery device that may comprise a plurality of arms disposed around the surgical retractor, and delivering the fluid may comprise delivering the fluid from a plurality of holes disposed in at least some of the plurality of arms.

The first fluid delivery or fluid evacuation device may comprise a fluid evacuation device that may comprise a plurality of arms disposed around the surgical retractor, and evacuating the fluid may comprise evacuating the fluid via a plurality of holes disposed in at least some of the plurality of arms. The first fluid delivery or fluid evacuation device may be a fluid delivery device and fluid may be stored in the fluid delivery device, and delivering the fluid may comprise releasing the stored fluid. The fluid may be delivered without requiring coupling of the fluid delivery device with an external source of fluid. The stored fluid may be stored in an absorbent material. Delivering the fluid may comprise delivering saline or an antibiotic to the surgical field.

The first fluid delivery or fluid evacuation device may further comprise an inner layer of material and an outer permeable layer, and the method may further comprise providing a support element disposed between the inner layer and the outer layer of material. The support element may provide support to prevent collapse of the layers inward toward one another. The method may further comprise providing a second fluid delivery or fluid evacuation device, and coupling the second fluid delivery or fluid evacuation device with the surgical retractor. The method may further comprise delivering fluid to the surgical field from the first fluid delivery device, and evacuating fluid from the surgical field with the second fluid evacuation device. The method may further comprise heating or illuminating the surgical site.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8A and 8B illustrate a perspective view and a cross-sectional view of the bracelet in FIG. 5 coupled with a surgical retractor.

FIGS. 21A-21B illustrate fluid delivery through a hand port.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

The present invention will be described in relation to a fluid delivery or fluid evacuation device coupled to a surgical retractor. However, this is not intended to be limiting. One of skill in the art will appreciate that the devices, methods and systems described herein may be used in other applications.

Figure 1:
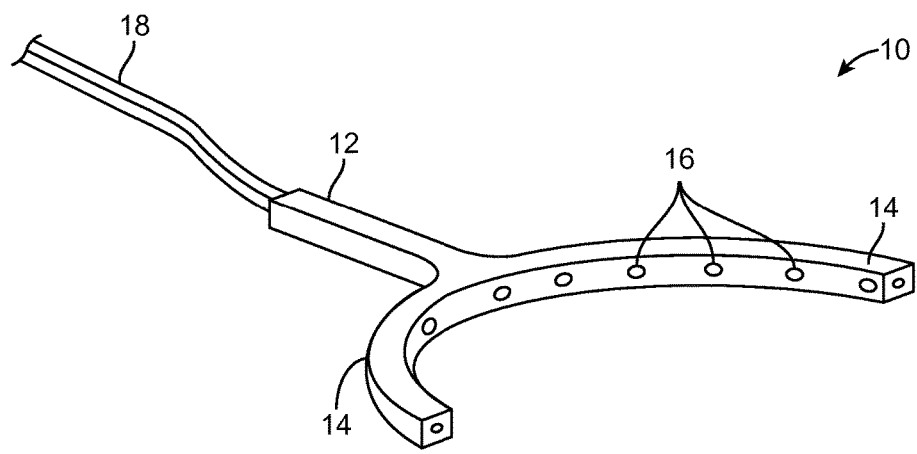
FIG. 1 illustrates an exemplary embodiment of a fluid delivery or fluid evacuation device.
Figure 2:
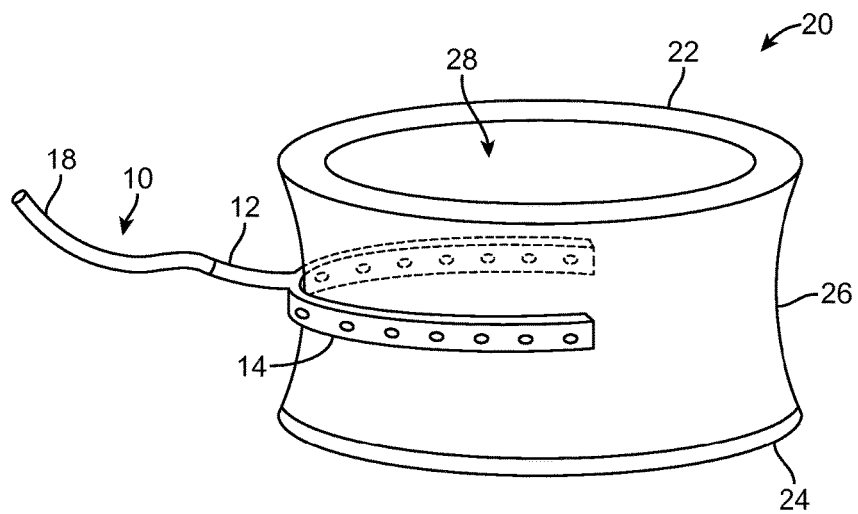
FIG. 2 illustrates the embodiment of FIG. 1 coupled to a surgical retractor.

FIG. 1 illustrates an exemplary embodiment of a fluid delivery or fluid evacuation device 10. The device 10 includes a pair of arcuate arms 14 that form a horseshoe-like or wishbone shape. An input 12 is coupled to the arms 14 and a tube 18 is coupled to the input 12. One or more holes 16 may be disposed along any portion of the plurality of arms 14. A lumen (not shown) extending through the arms fluidly couples the holes with the input 12. The arms 14 may be a rigid material or they may be resilient. In use, the fluid delivery or fluid evacuation device 10 is disposed adjacent a surgical incision, and preferably inserted through the incision at least partially into the surgical field. Fluid from an external source is delivered through the tube 18 into the input 12 and then distributed along the arms 14. The fluid then exits the holes 16 in the arms and trickles downward into the surgical field thereby wetting the surgical margins. The fluid may be any fluid including saline, an antibiotic, or any other therapeutic agent. The fluid may help keep the tissue moist during the surgical procedure as well as having other therapeutic effect such as killing bacteria to prevent infections. Instead of a fluid, a vacuum may be delivered through tube 18 and through input 12 to arms 14. The suction then evacuates fluids from the surgical site via holes 16. In still other embodiments, both fluid and vacuum may be delivered using device 10. This is variation, the device 10 will have one or more separate fluid delivery paths and one or more separate vacuum paths for fluid evacuation. In still another embodiment, two or more devices 10 may be used, one for fluid delivery and one for vacuum. In a preferred use, the device 10 may be coupled to a commercially available retractor 20 as seen in FIG. 2. An alternative embodiment of device 10 may include two arms that snap together around the retractor to form the finished device which may have a horseshoe shape or any other shape such as a closed circle or other shape.

Referring now to FIG. 2, the surgical retractor 20 includes an upper retention member such as a ring 22, a lower retention member such as a ring 24, and a pliable membrane 26 disposed therebetween. A channel 28 allows a surgeon to access the surgical field. The curvature of the arms 14 may substantially match the curvature of the pliable membrane. The fluid delivery or fluid evacuation device 10 is disposed under the upper ring 22 and at least partially surrounds the pliable membrane 26

Figure 3A:
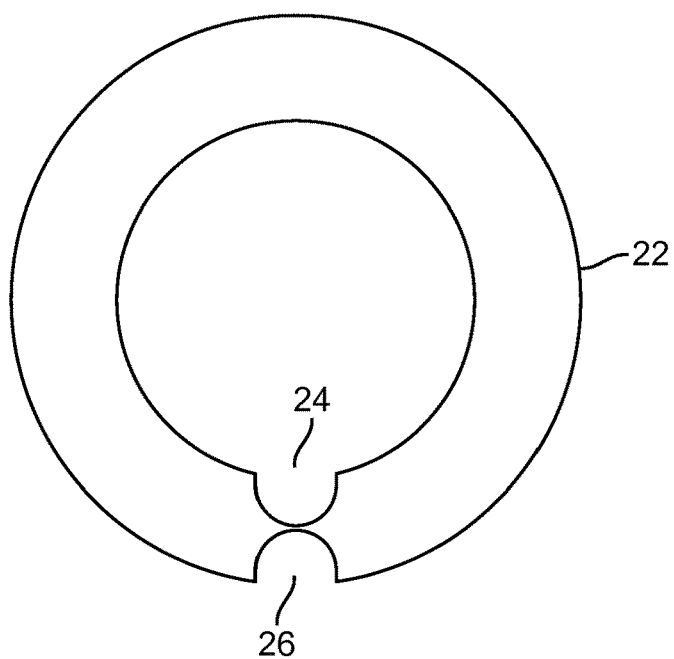
FIGS. 3A-3B illustrate an exemplary embodiment of a receptacle in either a surgical retractor or a fluid delivery or fluid evacuation device.
Figure 3B:
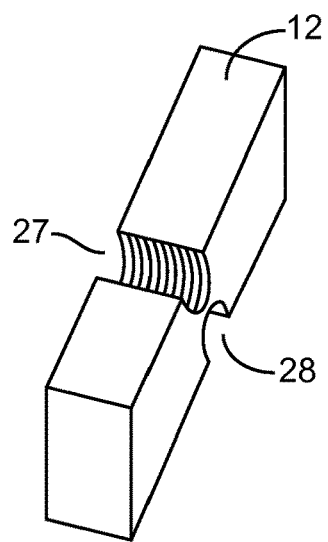

In a variation of the embodiment in FIG. 1, a notch or receptacle may be disposed in either the fluid delivery or fluid evacuation device, or the receptacle may be disposed in the surgical retractor. FIGS. 3A-3B illustrate exemplary embodiments of a receptacle.

In FIG. 3A, the upper retention member 22 of surgical retractor 20 includes a notch or receptacle 24 for receiving the input 12 of the fluid delivery or fluid evacuation device 10. The receptacle allows the input 12 to be disposed therein when the two devices are coupled together thereby reducing the overall profile of the two devices at their engagement point. This allows the devices to maintain a flat profile. Also, this reduces the pressure on the patient's skin and the risk of fluid leaking onto the skin during use. Optionally, a second receptacle 26 may be disposed on the opposite side of the first receptacle 24 thereby allowing engagement of device 10 on either side of the retention member 22.

FIG. 3B illustrates an alternative embodiment where the notch or receptacle 27 may be disposed on the input 12 of device 10 instead of being on retention member 22. An optional second receptacle 28 may be disposed on the opposite side of input 12 to allow engagement on either side of the input 12. Another variation includes notches on both the device 10 and the retractor 20.

Figure 4:
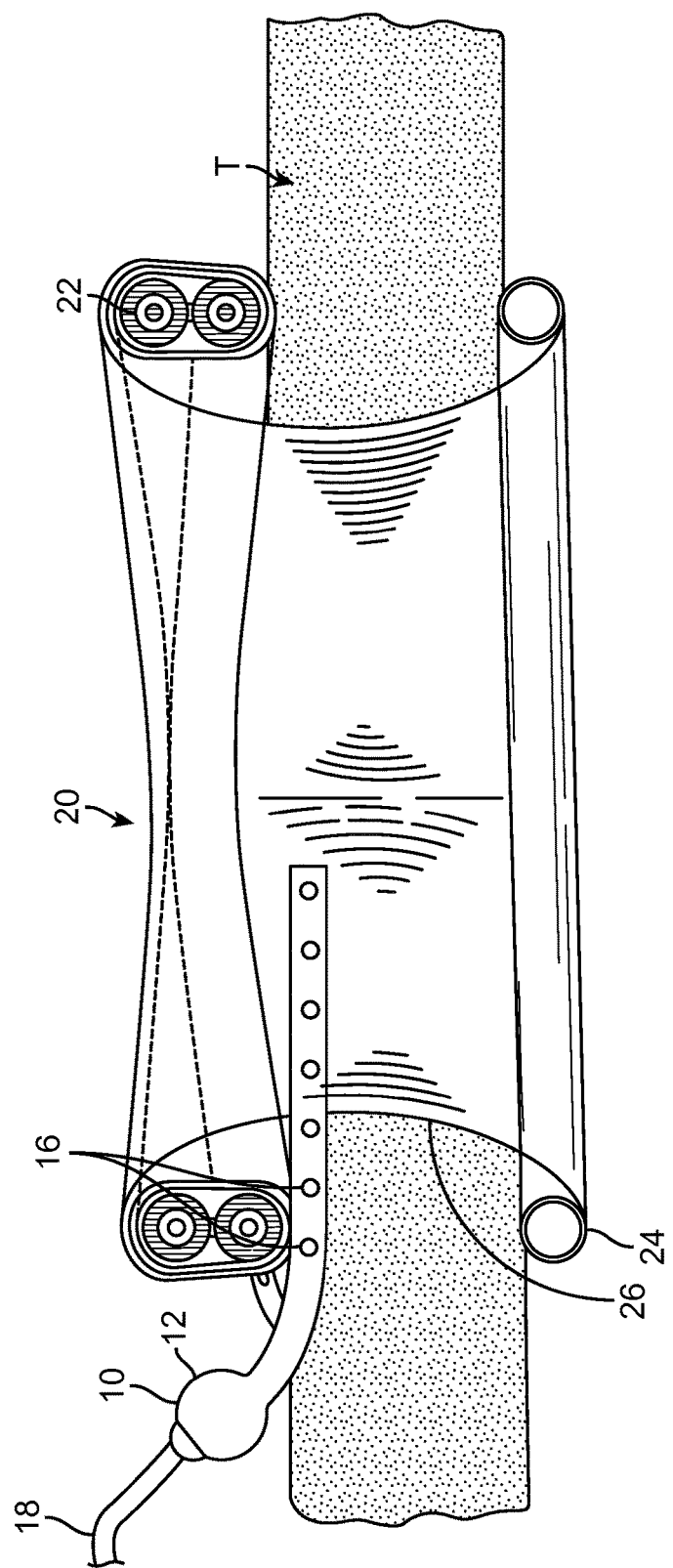
FIG. 4 illustrates a cross-section of a fluid delivery or fluid evacuation device and a surgical retractor disposed in a patient.

FIG. 4 illustrates a cross-section of device 10 coupled to surgical retractor 20 disposed through an incision in a patient's skin T. The fluid delivery or fluid evacuation device is captured between the upper ring 22 and the patient's skin. The bottom ring 24 is disposed under the skin. The upper ring 22 may be rolled up to tension the pliable membrane 26 thereby retracting the incision and further capturing device 10. Fluid delivery device 10 is now configured to deliver fluid along the outside of the pliable membrane 26. If a second fluid delivery or fluid evacuation device 10 is used (not illustrated) and coupled to a vacuum source, both fluid delivery and fluid evacuation will occur.

Figure 6:
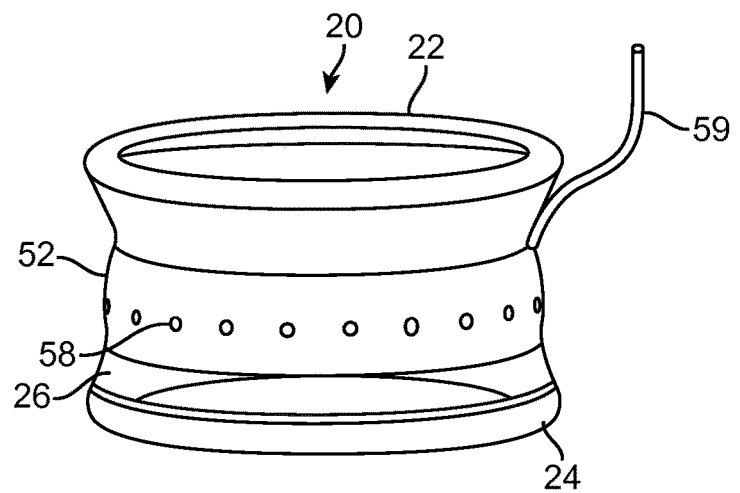
FIG. 6 illustrates an exemplary embodiment where the bracelet of FIG. 5 is coupled to a surgical retractor.

FIG. 6 illustrates another exemplary embodiment of a fluid delivery or fluid evacuation device 52. The device 52 is a bracelet preferably forming a closed ring having an inner surface 54 and an outer surface 56. One or more holes 58 are disposed in the outer surface 56 to allow fluid delivery or fluid evacuation therefrom. A tube 59 is coupled to the device 52 and allows coupling with a source of fluid or a vacuum. The outer surface 56 is preferably formed from a first layer of material and the inner surface is preferably formed from a second layer of material. The two layers are joined together either by welding, adhesive or chemical bonding, or by other techniques known in the art. A channel is formed between the layers thereby allowing fluid or vacuum to pass through the bracelet and out the holes 58. Some of the components are preferably resilient in order to prevent collapse of the device under the forces generated during wound retraction. Additionally, a fluid dispersion member, for example a separate conduit having low flow resistance about its longitudinal axis may be disposed within the channel that fluid is evenly distributed about the circumference of the bracelet.

The device in FIG. 6 is preferably coupled with a surgical retractor as illustrated. The bracelet 52 is disposed around the circumference of the pliable membrane 26 of surgical retractor 20. The two are preferably coupled together before placing the surgical retractor in the patient. Fluid is delivered from a fluid source via tube 59 to bracelet 52. The fluid exits holes 58 to deliver the fluid to the margins of the surgical incision. In other embodiments, fluid may be substituted with a vacuum to evacuate fluids from the surgical site. In still other embodiments, the bracelet may have both fluid delivery and fluid evacuation channels.

Figure 7:
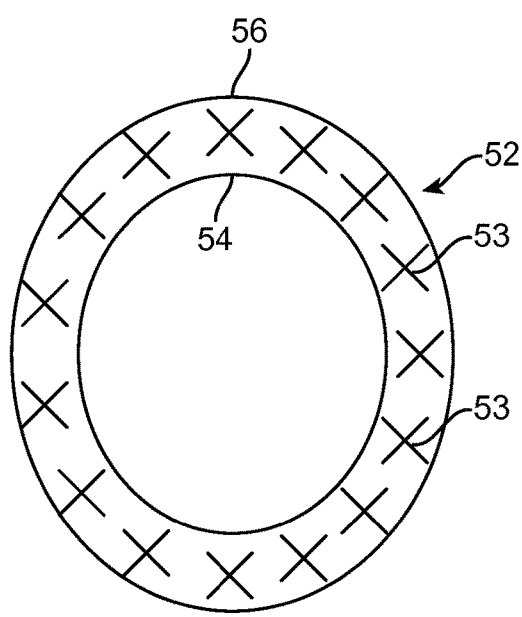
FIG. 7 illustrates a support element in a fluid delivery or fluid evacuation device.

In still other embodiments, a second bracelet (not shown) may be disposed around the surgical retractor and thus one bracelet may be used for fluid delivery and the other bracelet may be used for fluid evacuation. In the embodiment used for fluid evacuation, the vacuum may cause collapse of the inner and outer layers of material toward one another. Therefore, a resilient material such as foam may be disposed between the two layers of material to provide support and prevent collapse. Exemplary foams include reticulated (open-cell) polyethylene or polyurethane foams. It should be apparent that this same structure could also be used for the fluid delivery bracelet, with the foam serving as the resilient structure configured to prevent collapse of the lumen. FIG. 7 illustrates a support structure 53 such as foam disposed between the inner and outer layers 54, 56 of material in bracelet 56.

FIG. 8A illustrates a perspective view and FIG. 8B illustrates a cross-sectional view of a bracelet 52 that has been slidably advanced over surgical retractor 20. In this embodiment, fluid is actively delivered to surgical site because fluid from an external source is delivered via tube 59 to bracelet 52. The fluid is then delivered to the surgical site via holes 58. In other embodiments that will be discussed later, the fluid may be passively delivered to the surgical site. The support structure 53 may optionally be included in the bracelet. Additional details about the surgical retractor are disclosed in U.S. Pat. No. 7,883,461.

Figure 9:
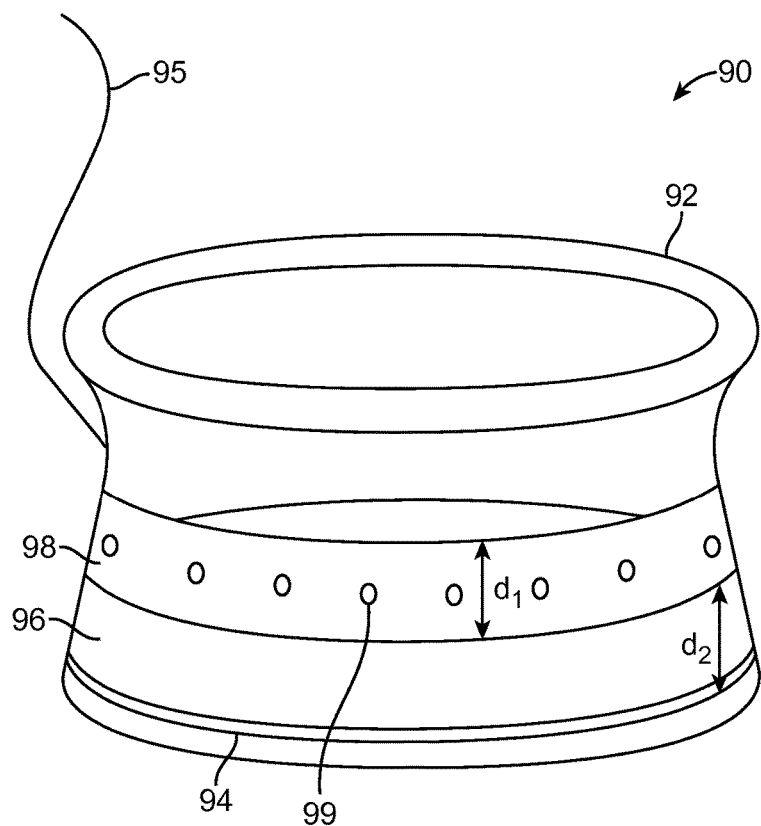
FIG. 9 illustrates a fluid delivery or fluid evacuation device integrally formed with the surgical retractor.

As discussed above, the bracelet may be a separate bracelet that is slidably advanced over the surgical retractor, or the bracelet may be a ring that is integrally formed with the surgical retractor. FIG. 9 illustrates an exemplary embodiment where the bracelet is integrally formed with the surgical retractor. The combined surgical retractor and fluid delivery or fluid evacuation device 90 includes an upper retention member or ring 92, a lower retention member or ring 94 and a pliable membrane 96 disposed therebetween. The fluid delivery or fluid evacuation device 98 is an outer ring that is coupled to pliable membrane 96. Holes 99 in the ring 98 allow fluid or suction to be delivered therefrom. This embodiment is an active fluid delivery system therefore fluid is supplied from a fluid source via tube 95 to the ring 98. The ring 98 in this embodiment encircles the entire circumference of the pliable membrane 96 which is cylindrically shaped. The width of the ring 98 is represented by $d_1$ and it is disposed a distance $d_2$ from the bottom ring 94.

It is generally undesirable deliver fluid along substantially the entirety of the wound margins, which is common in a number of commercially available devices. This is because fluid may undesirably leak onto the skin, into the abdomen, or otherwise be delivered to non-target layers of the surgical wound. In particular, it is desirable to limit fluid delivery to layers of adipose tissue, avoiding areas that are highly vascularized, limiting systemic absorption. Using a proprietary wound model described in U.S. patent application Ser. No. 14/209,393 which is incorporated herein by reference, $d_1$ is preferably in the range from about 0-3 inches, and more preferably about 1 inch. Additionally, $d_2$ is in preferably in the range from 0-2 inches, and more preferably about 0.75 inches. These dimensional characteristics maximize compatibility with the wide range of patient abdominal wall thicknesses encountered during surgical practice, minimize the amount of fluid that leaks into the abdominal cavity and/or out onto the skin, and provide room to roll the top ring and shorten the length of the pliable membrane, thereby effectively retracting the surgical wound. This feature can be a drawback in dual layer designs because fluid connections to the device can impede performance of the surgical retractor since tubes may interfere with the ability to roll the top ring and achieve satisfactory wound retraction. The embodiment of FIG. 9 overcomes this challenge.

One of skill in the art will also appreciate that any of the features previously described above with respect to the slidable bracelet embodiment may be applied to the embodiment of FIG. 9 as well. For example, support structures for preventing collapse of material layers, fluid dispersion members, etc. may be included. Additionally, the embodiment of FIG. 9 may be used to provide suction to the wound instead of fluid delivery, or the device may have separate channels to provide both suction and fluid delivery.

Figure 10:
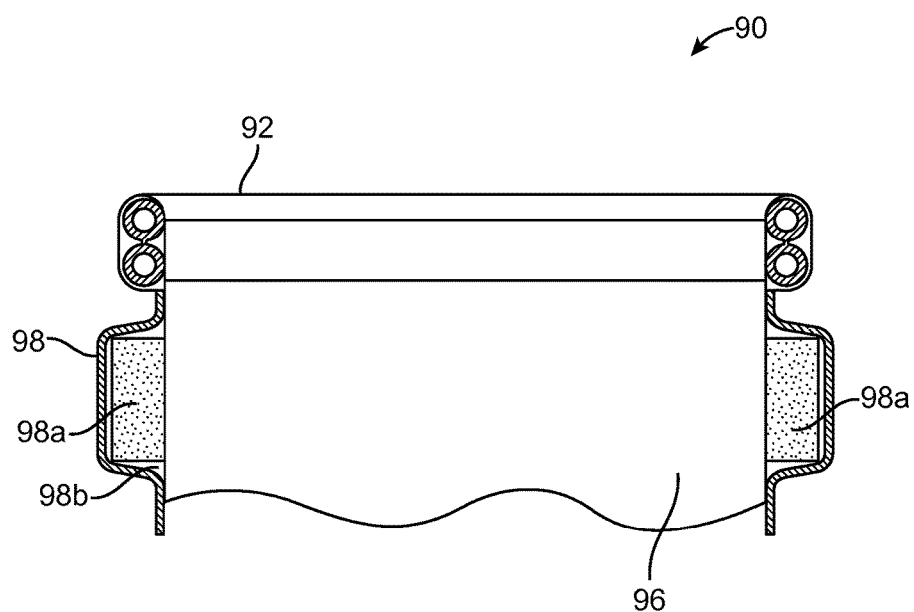
FIG. 10 illustrates a cross-section of FIG. 9.

FIG. 10 illustrates a cross-section of the integral fluid delivery or fluid evacuation device seen in FIG. 9. An outer layer of material 98 is coupled to the pliable membrane 96 to form a channel 98b in which fluid may pass or through which a vacuum may be applied. The two layers may be sealed with one another by any number of techniques including thermal welding, solvent bonding, adhesive bonding, or other techniques known in the art. An optional support structure 98a such as foam may be disposed in the channel 98b to prevent the channel from collapsing during retraction, as well as to support the channel when suction is delivered through the channel. The upper ring 92 preferably has major axis that is different than the minor axis in order facilitate rolling of the upper ring. Having the two different axes locks the upper ring in position during rolling and prevents unwrapping of the pliable membrane 96. As previously discussed, fluid delivery or vacuum may be delivered using this embodiment. Fluid may be actively delivered to this embodiment, or it may be passively delivered as will be disclosed below.

The active fluid delivery system described above includes a fluid delivery tube that is provided to the surgeon pre-connected to the fluid delivery or fluid evacuation device. It is also contemplated that the tube maybe provided disconnected and the surgeon or operating room assistant may couple the two together during the procedure.

Figure 5:
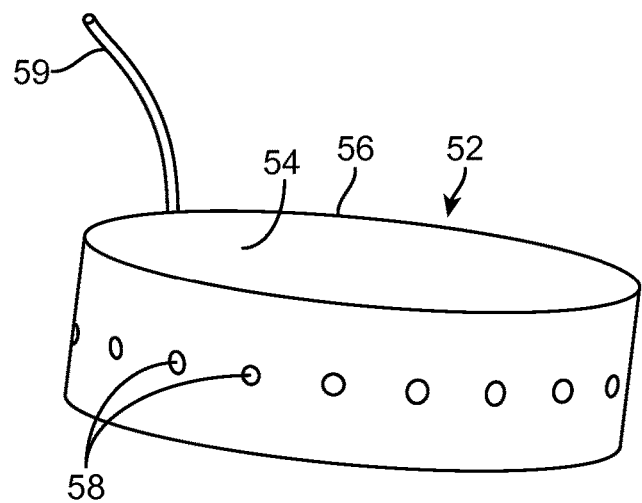
FIG. 5 illustrates an exemplary embodiment of a bracelet.

As mentioned above, the bracelet embodiment in FIG. 5 or the integral embodiment in FIG. 9 may provide fluid delivery passively instead of actively. In these embodiments, the structure of the devices is substantially the same except that a tube is not required for coupling with a fluid source. Additionally, an absorbent material such as foam is preferably disposed in between the inner and outer layers of material of the bracelet or the integral ring. The absorbent material may be loaded with fluid such as saline or antibiotic before or during the surgical procedure, and the fluid disperses from the foam into the wound during the procedure. Thus, the embodiment in FIG. 10 illustrates this exemplary embodiment. This embodiment also preferably either does not provide suction for fluid evacuation, or it is provided with a separate bracelet or separate integral ring.

The passive delivery device preferably includes a permeable membrane (e.g. polyurethane with laser-drilled holes) that is heat-sealed or RF welded to the pliable membrane, defining an enclosed volume having an absorbable material disposed therein. The structure might also be formed by constructing a band having an adhesive backing that permits attachment about the circumference of the pliable membrane before use. The absorbent material such as a foam band may be substantially desiccated and in a collapsed, minimum thickness configuration upon manufacture, but can be soaked in a fluid (e.g. antibiotic, antiseptic, biologic, therapeutic agent, etc.) before use to absorb a defined volume of fluid. The preferred volume of fluid absorbed is about 5 to about 500 mL of fluid, but any volume may be used based on the effective amount required. Once placed in the surgical wound, the fluid is slowly released into the surgical wound through the permeable and pliable membrane.

Use of a passive delivery system described above may involve the following method which includes opening the product package, adding fluid, deploying the device into the wound and retracting tissue. Fluid may be added by submerging the device in a bath of desired fluid or injecting the desired fluid into the defined volume using a syringe. Optionally, additional fluid may be added later during the procedure.

Alternatively, the device may be pre-packaged with the desired fluid, eliminating the need for the step where fluid is added or replenished.

In alternative embodiments, a second absorbent layer of material may be incorporated into the device in order to absorb excess fluid. For example, the second fluid retention member or second absorbent layer of material could be constructed from an absorbent fabric or hydrogel to capture excess fluid.

Figure 11:
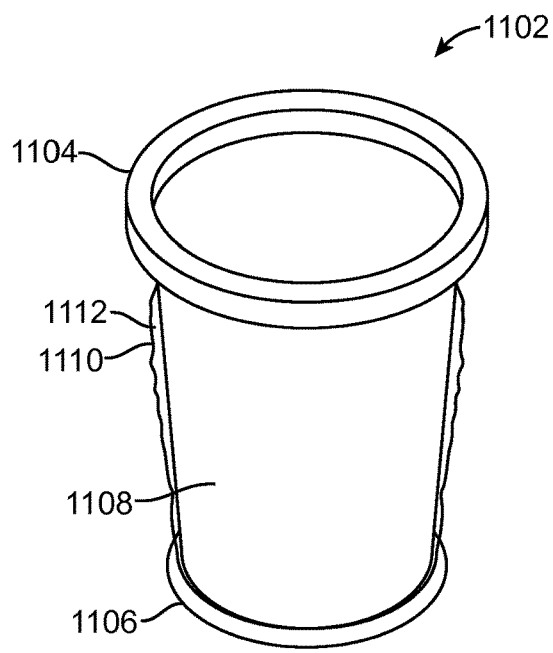
FIG. 11 illustrates another exemplary embodiment of a fluid delivery or fluid evacuation device.
Figure 12:
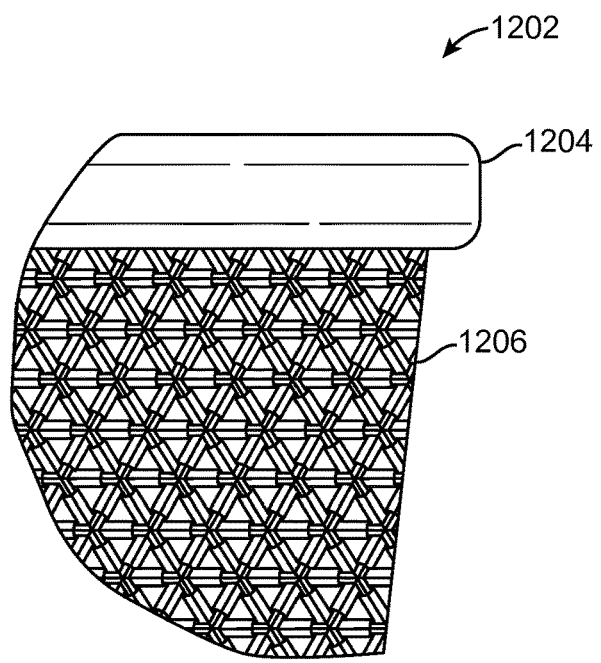
FIG. 12 illustrates the use of an absorbent layer in a fluid delivery or fluid evacuation device.

The embodiments previously described have a narrow band where fluid may be delivered or where fluid may be evacuated. Alternatively, as shown in FIG. 11, instead of confining the fluidic delivery surface to a specific region, the entire surface of the "passive delivery" system might be capable of absorbing and releasing fluid. Thus, the device 1102 includes an upper retention member 1104 such as a ring, a lower retention member 1106 such as a ring and a pliable membrane 108 disposed therebetween. An outer permeable layer of material 1110 is coupled to the pliable membrane thereby forming a pocket 1112 in which fluid may be stored for delivery, or in which fluid may be collected during fluid evacuation. Thus fluid may be delivered along the entire length and circumference of the permeable membrane. Other aspects of the device 1102 are similar to those previously disclosed such as the use of an absorbent material, pre-loading of the fluid, etc. The device in FIG. 11 is not limited to passive fluid delivery or passive fluid evacuation. In alternative embodiments, the device may also be connected to an external fluid source to convert it to an "active delivery" system for fluid or suction. Additionally, one of the layers in the device such as the pliable membrane 1108 or the permeable layer 1110 may be fabricated from an absorbable material that can store the fluid. Preferably volumes include 5 to about 500 mL of fluid that is slowly released to the surgical site, or that is absorbed during the procedure. Thus, in this embodiment only one layer of material is required in the device, although both layers may be included. FIG. 12 illustrates the single layer of absorbent material 1206 coupled to upper retention member 1204 in a fluid delivery or fluid evacuation device 1202.

Figure 13:
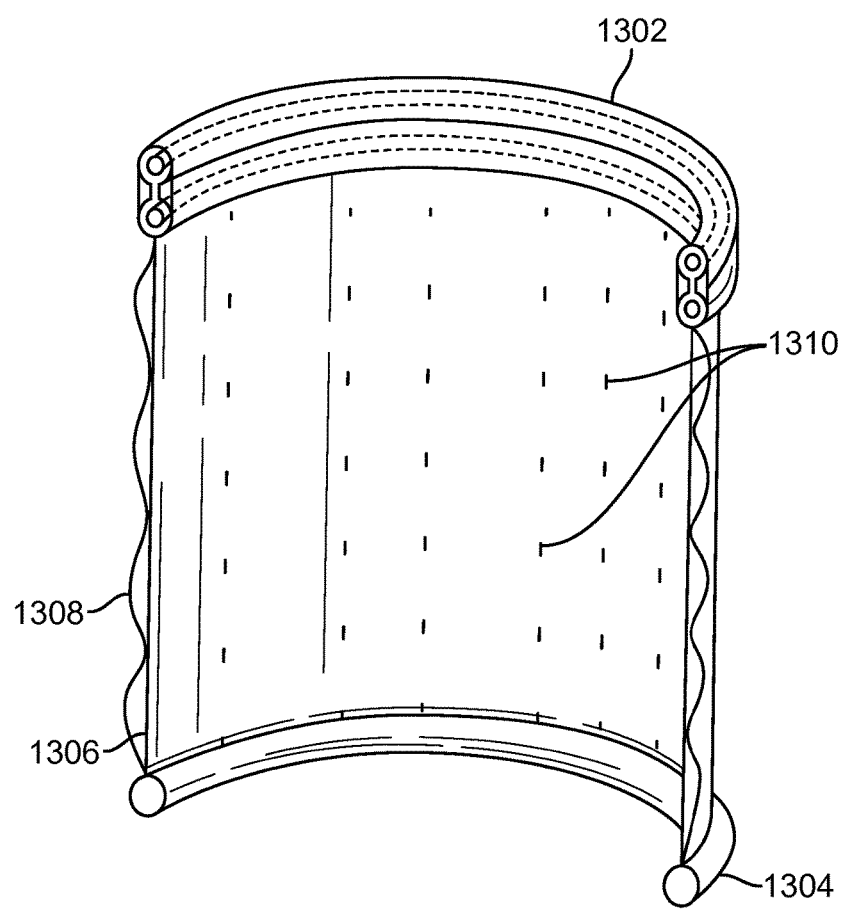
FIG. 13 illustrates the use of a quilted pattern between layers.

FIG. 13 illustrates the use of welding to create a quilted pattern 1310 in any of the double layer embodiments disclosed herein. This embodiment includes an upper retention member 1302 or ring, a lower retention member 1304 or ring, an inner layer of material 1306 and an outer layer of material 1308. In order to prevent fluid from ballooning the dual membrane structure and obscuring the surgical field/view, it may be desirable to incorporate "quilt seals" 1310 into the design to limit the maximum volume to which the structure can expand. These seals are shown as a pattern of repeating seals along the longitudinal axis and circumference of the cylindrical sheath between layers 1306 and 1308.

Additionally, because it is well known that maintaining wound normothermia can reduce the incidence of wound infections, the volume defined by any of the inner/outer layers of any of the devices described herein may also incorporate chemicals that would undergo an exothermic reaction to warm the wound. For example, anhydrous copper sulfate might be disposed in the volume such that when fluid is delivered to the volume (for any embodiment disclosed herein), the combination of water and the anhydrous copper sulfate creates a mild warming effect that may reduce the risk of wound infection.

Furthermore, in embodiments where fluid evacuation is included, surgeon feedback has suggested that the "gurgling" noises created can be distracting. Hence it may be beneficial to time cycle the suction so that air trapped in the suction system is minimized, minimizing noise. Further yet, foam disposed within a substantial length of the suction plumbing will also help minimized noise that results from the suction.

Also, given the constraints of the operating room, it can be undesirable to have large flow rates of fluid into the surgical wound or space, even if this fluid is removed (primarily because in an open loop system, the fluid supply would have to be replenished frequently). To solve this issue, a circulating system may be included with the devices disclosed herein, and this can be used to re-deliver fluid removed from the wound back into the wound. Because this approach might have issues with contamination, it is further desirable to limit the fluid flow to the wound using fluid control valves defining an adjustable orifice and/or check valves to limit the flow in one direction.

Figure 14:
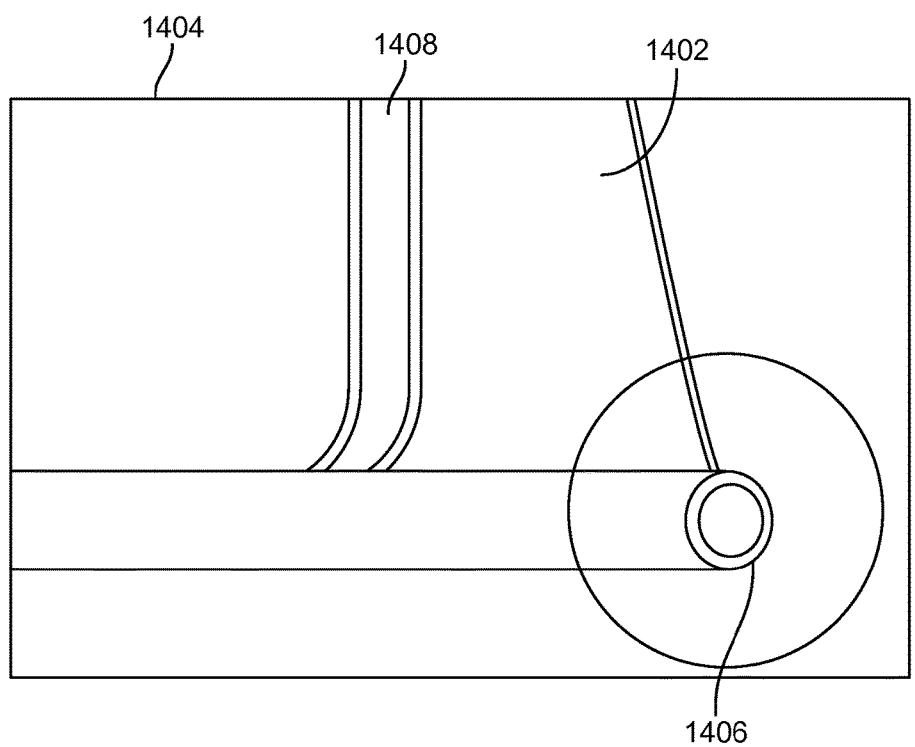
FIG. 14 illustrates a feature for helping to eliminate leakage.

FIG. 14 illustrates a feature for helping to eliminate fluid leakage. The fluid delivery or fluid evacuation device may be any of the embodiments disclosed herein and it may be combined with any of the surgical retractors disclosed herein. The device includes an outer layer of material 1402 and a plurality of holes 1404 disposed therein for delivering the fluid. A gutter or channel 1406 may be disposed at or near the bottom of the device, preferably in the lower retention member or ring, in order to collect fluid which can be evacuated via a suction channel 1408. This feature is advantageous since leakage of the fluid onto the skin is a problem described previously herein. The gutter 1406 is capable of removing fluid that reaches the bottom ring through a small annular opening. Fluid can then be removed from the bottom ring through a tube connected to suction. By removing fluid from the wound space, the chance of fluid leaking onto the skin is minimized.

Another technique for preventing skin leakage is to provide a barrier between the device and the skin, effectively creating a seal at the skin to device interface. This may be embodied by a silicone or polyurethane gasket or bumper disposed between the bottom surface of a top ring (or retention member) and the skin.

Any of the active or passive fluid delivery or fluid evacuation embodiments may also be incorporated into a surgical retractor having an expanding ring retraction design such as disclosed in U.S. patent application Ser. No. 13/736,904, the entire contents of which are incorporated herein by reference. In addition to serving as a wound retractor, it may be beneficial to provide means of maintaining and delivering fluid to the wound tissue. This fluid may be a normal saline solution or an antibiotic solution and serve the function of keeping the wound tissue moist during surgery as well as destroy any bacteria that are able to get into the wound space.

Figure 15:
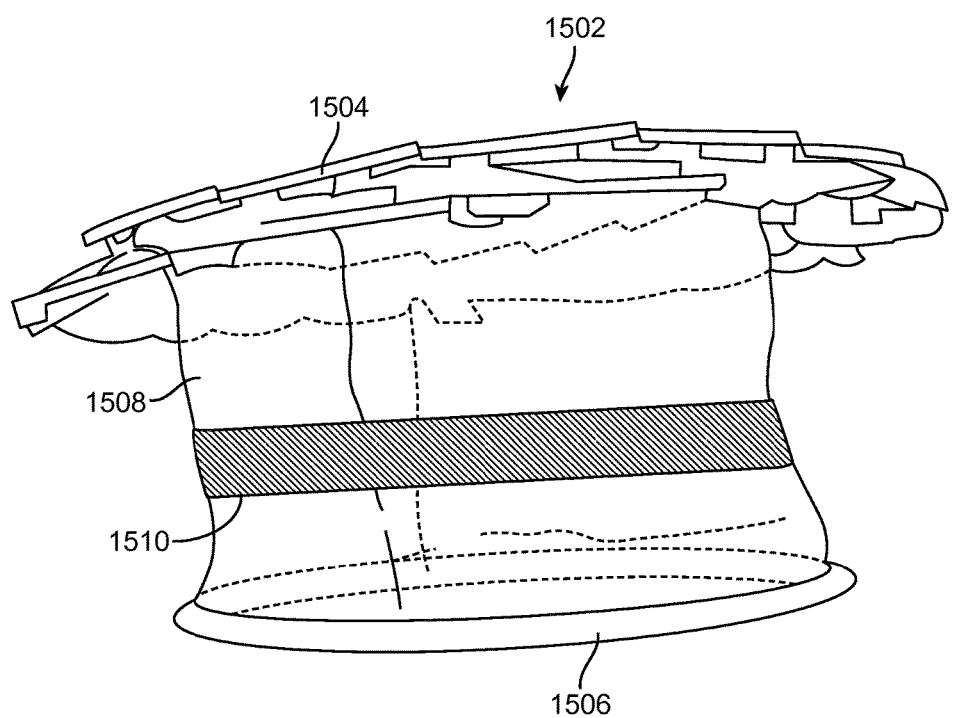
FIG. 15 illustrates an exemplary surgical retractor with expandable upper ring and a fluid delivery or fluid evacuation device.

FIG. 15 illustrates a surgical retractor 1502 with a bracelet 1510 disposed thereover. The bracelet 1510 may be any of the bracelet embodiments previously described, including those for active fluid delivery or active fluid evacuation, or for passive fluid delivery or passive fluid evacuation. The device includes an outer layer of material 1508 against which the bracelet 1510 is disposed. The upper expandable retention member or ring 1504 is described in greater detail below. Lower retention member or ring 1506 is preferably a resilient ring. Expansion of the upper ring 1504 retracts the incision, and collapsing the upper ring relaxes the incision to an unbiased configuration. Other aspects of the bracelet generally take the same form as previously described in other embodiments.

Figure 16:
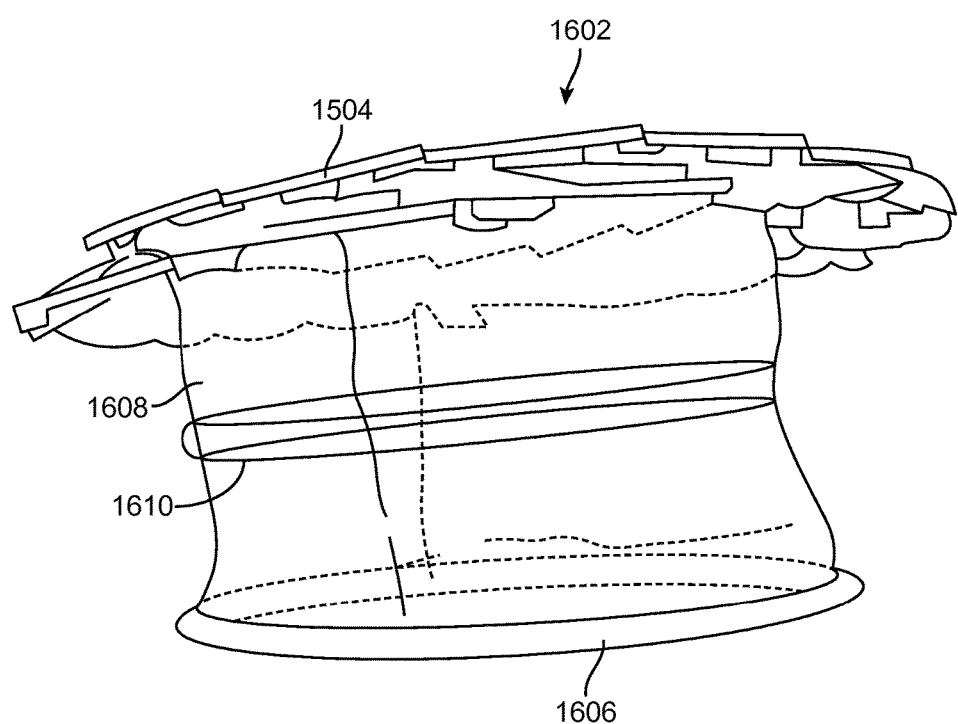
FIG. 16 illustrates an exemplary surgical retractor with expandable upper ring and an integral fluid delivery or fluid evacuation device.

FIG. 16 illustrates an embodiment similar to that in FIG. 15, with the major difference being that instead of a separate bracelet that is slidably disposed over the pliable membrane, in this embodiment the bracelet is integrally formed with the pliable membrane. The surgical retractor 1602 includes an upper expandable retention member or ring 1504 that is described in more detail below, a lower retention member or ring 1606 and a pliable membrane 1608 disposed therebetween. The bracelet 1610 is integrally formed with the pliable membrane 1608 using techniques previously disclosed above such as by sealing an outer layer of material to the pliable membrane. The integral bracelet may be active or passive with respect to fluid delivery or fluid evacuation as previously disclosed.

Figure 17:
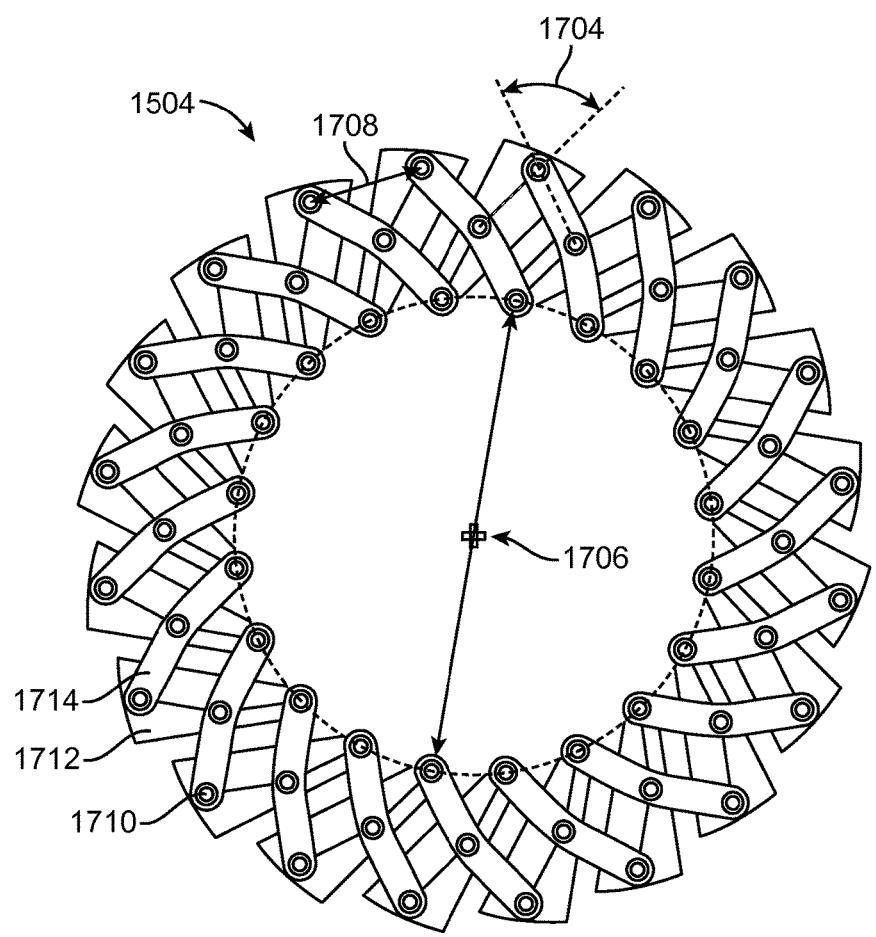
FIG. 17 illustrates an exemplary upper expandable retention member.

FIG. 17 illustrates an exemplary embodiment of the expandable upper retention member 1504 in greater detail. The upper ring 1504 includes a plurality of upper 1714 and lower links 1712 that are pivotably coupled together with a pin 1710 to form a closed ring having an inner diameter 1706. As the ring is expanded, the diameter 1706 increases and the distance between pins 1708 also increases while the angle between pins 17054 decreases. When the ring is collapsed, the diameter 1706 decreases and distance 1708 also decreases while angle 1704 increases. Thus, the upper ring can be joined to the pliable membrane to expand the pliable membrane and retract an incision. A locking mechanism such as a ratchet and pawl or a clasp may be used to lock the ring into a desired configuration.

Figure 18A:
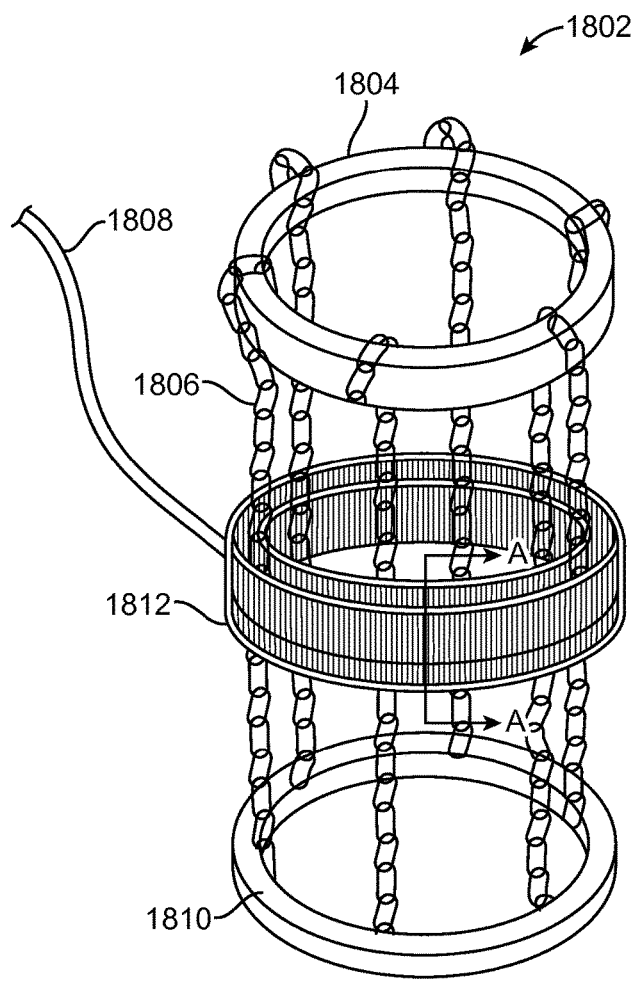
FIGS. 18A-18B illustrate an exemplary embodiment of a surgical retractor with a fluid delivery or fluid evacuation device.
Figure 18B:
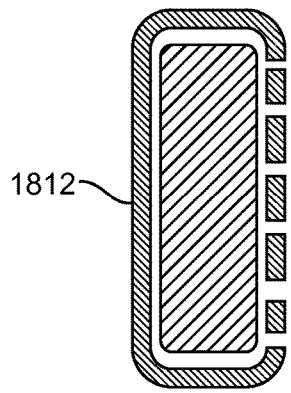

Referring now to FIGS. 18A-18B, the active and/or passive fluid delivery systems described previously may be incorporated into another embodiment of the dual ring wound retractor designs previously described above. The device 1802 includes an upper ring 1804, a lower ring 1810 and a plurality of chain links 1806 replaces the pliable membrane in previous embodiments. An optional tube 1808 couples the bracelet 1812 with a fluid source or vacuum source. Thus, the device may retract tissue and deliver fluid and optionally suction the fluid from the surgical site as well. FIG. 18B shows section A-A which is a cross section of the bracelet which may include inner impermeable layer, and outer permeable layer and a foam or other absorbent material disposed therebetween for providing support, or for absorbing fluid, or for providing the fluid.

Figure 19:
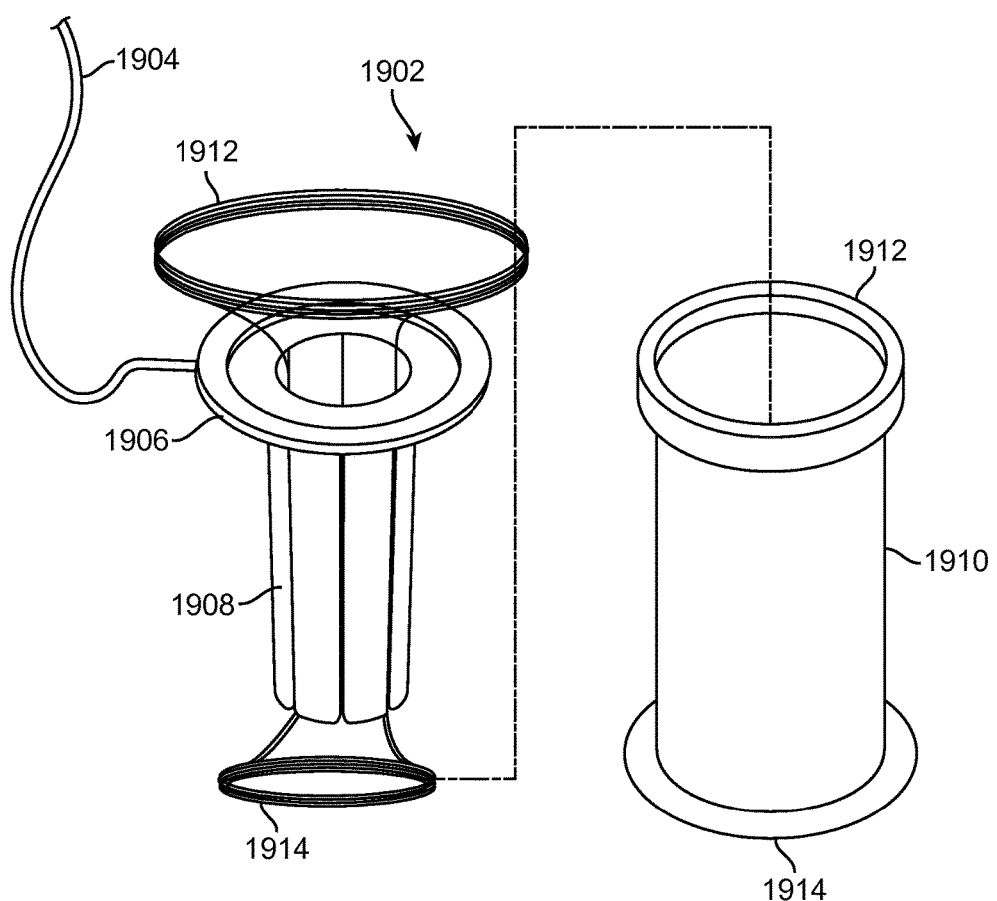
FIG. 19 illustrates an exemplary embodiment of yet another surgical retractor with a fluid delivery or fluid evacuation device.

Similarly FIG. 19 provides an alternative embodiment of the bracelet design configured to be used with the dual ring retractor design previously described above. The device 1902 includes an upper ring 1912, a lower ring 1914 and a pliable membrane 1910 therebetween. The fluid delivery or fluid evacuation device includes an upper flange 1906 and a plurality of fingers 1908 extending axially outward from the flange 1906. The fluid delivery or fluid evacuation device may be disposed over the retractor such that the fingers extend circumferentially around the pliable membrane and substantially along the entire length of the pliable membrane. The fingers ensure delivery and optionally removal of fluid from substantially the entire depth of the wound.

Figure 20:
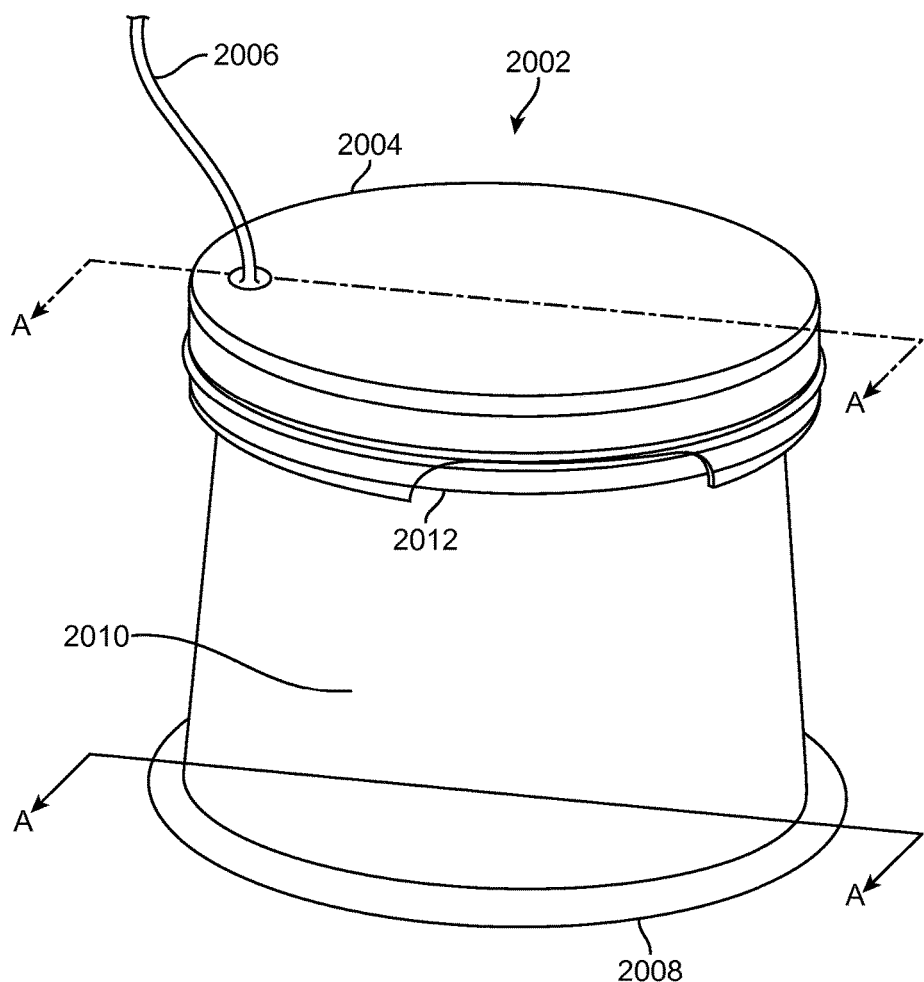
FIG. 20 illustrates fluid delivery or fluid evacuation with a hand port device.

The fluidic systems previously described can also be incorporated into the design of hand port devices previously described in the patent literature, for example the Gel-Port described in U.S. Pat. No. 7,883,461. FIG. 20 illustrates an embodiment of a hand port device with fluid delivery or fluid evacuation. The device 2002 includes a hand port 2004 coupled to an upper retention ring 2012. The device also includes a lower retention ring 2008 and a pliable membrane 2010 coupled to both rings. A tube 2006 is coupled to the device to either deliver fluid or to evacuate fluid as will be described below. The hand port 2004 includes a resilient material that easily allows a surgeon's hand to penetrate and pass through the port, and upon removal of the hand, the resilient material substantially returns to a relaxed configuration and the penetration is substantially closed.

The tube is fluidly coupled to the hand port such that fluid travels along the annulus of the hand port the outside surface of the pliable membrane, thereby irrigating the surgical wound, and possibly also disinfecting the wound when an antiseptic fluid (e.g. antibiotics) is used. Alternatively, the fluidic system can be configured to deliver antibiotic fluid or other fluid directly to the hand port such that the surgeon's hand is lubricated and disinfected with each pass in and out of the abdomen. FIG. 21 illustrates fluid delivery around the annulus of the hand port and FIG. 21B illustrates fluid delivery directly to the hand port.

Figure 22:
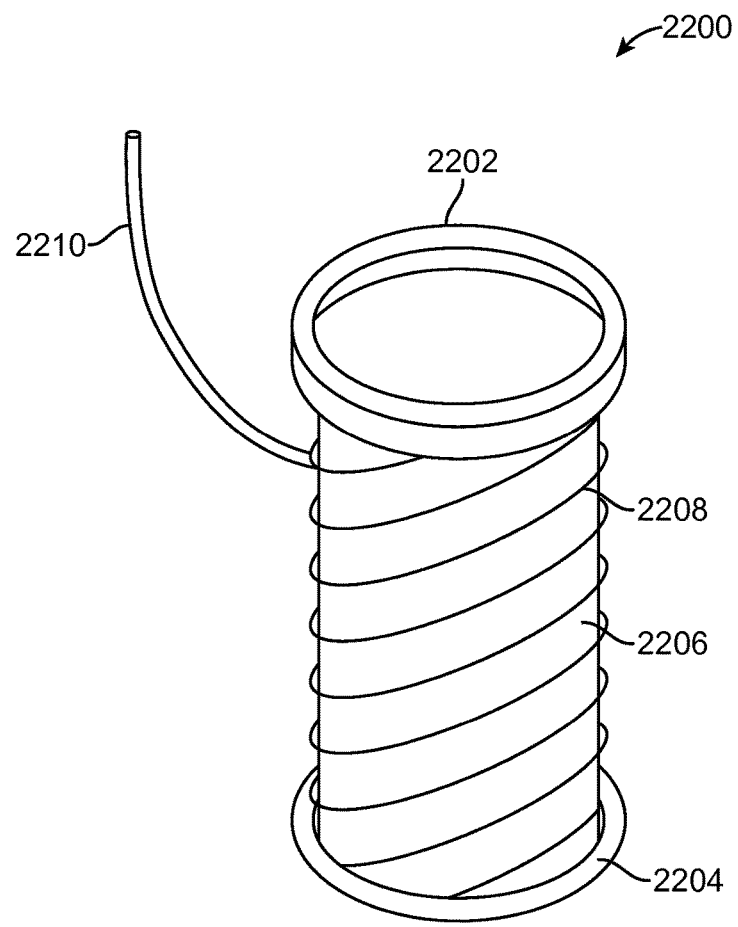
FIG. 22 illustrates a surgical retractor with spiral fluid delivery or fluid evacuation.

FIG. 22 illustrates still another exemplary embodiment of a surgical retractor with fluid delivery or fluid evacuation. The device 2200 includes an upper ring 2202, a lower ring 2204 and a pliable membrane 2206 disposed therebetween. A spiral tube 2208 is disposed along the outer surface of the pliable membrane and is permeable and can either deliver fluid to the surgical site or evacuate fluid from the wound. A tube 2210 is coupled to a fluid source or a vacuum. In some embodiments both vacuum and fluid delivery are provided. The spiral may be pre-attached to the surgical retractor, or a surgeon may attach the spiral during the procedure.

Figure 23:
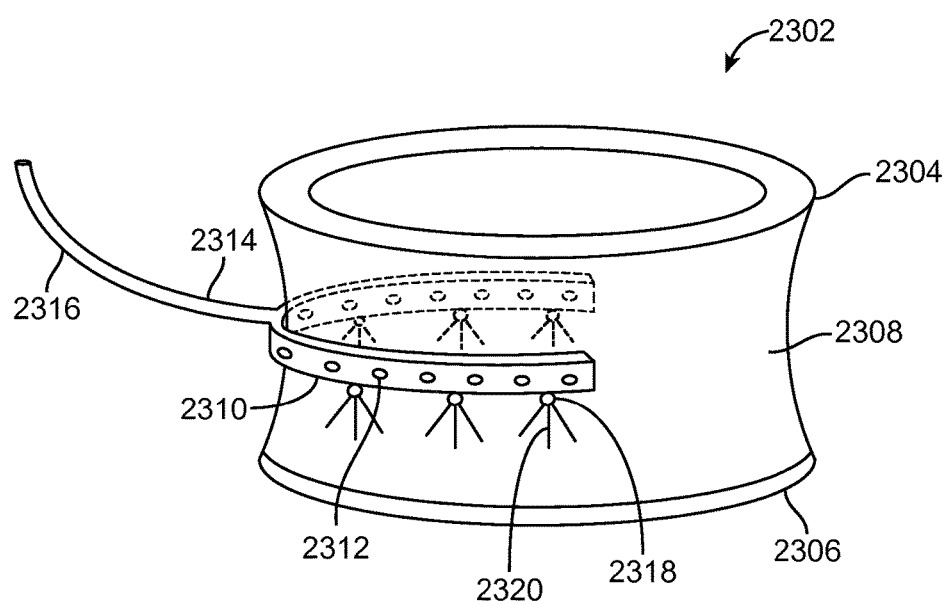
FIG. 23 illustrates an exemplary embodiment of a surgical retractor with fluid delivery or fluid evacuation and illumination elements.

Any of the embodiments disclosed herein may also include an illumination element such as a fiber optic cable, an LED, an incandescent light, or any other source of light for illuminating the surgical site. The light may also be an ultraviolet light to help sterilize the surgical site, or another wavelength known in the art to help maintain sterility. FIG. 23 illustrates an exemplary embodiment of an illuminated surgical retractor with fluid delivery or fluid evacuation. The device 2302 includes a surgical retractor which may be any of the embodiments disclosed herein, but in this example includes an upper retention member or ring 2304, a lower retention member or ring 2306 and a pliable membrane 2308 disposed therebetween. A fluid delivery or fluid evacuation device is coupled to the surgical retractor and may be any of the embodiments disclosed herein, but in this example includes a plurality of arcuate arms 2310 disposed around the pliable membrane. An input 2314 allows a tube 2316 to be coupled to the arms. The tube may be coupled to a source of fluid or to a vacuum. Holes 2312 in the arms allow fluid to be delivered or evacuated from the surgical site. Illumination elements 2318 are coupled to the arms and illuminate the surgical field with light, UV light, or other illumination 2320.

Also, any of the embodiments disclosed herein may include a hydrophilic coating disposed on either the surgical retractor or the fluid delivery or fluid evacuation device, but preferably on the pliable membrane portion of the surgical retractor. This coating helps more evenly distribute fluid delivered by the fluid delivery device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical access system adapted to facilitate access to a surgical site through an incision in a patient's body, said system comprising:
   a surgical retractor comprising an upper retention member, a lower retention member and a membrane disposed therebetween; and
   a first fluid delivery or fluid evacuation device coupled with the surgical retractor, the first fluid delivery or fluid evacuation device configured to deliver fluid to the surgical site or configured to evacuate fluid from the surgical site, wherein the first fluid delivery or fluid evacuation device forms a ring coupled to an outer surface of the membrane, the ring having a width d1 and the ring being disposed a distance d2 from the lower retention member,
   wherein d1 is greater than d2,
   and wherein d2 is non-zero.

2. The system of claim 1, wherein the upper retention member comprises an expandable and collapsible ring, and wherein the lower retention member comprises a resilient ring.

3. The system of claim 1, wherein the first fluid delivery or fluid evacuation device further comprises a fluid delivery or fluid removal tube fluidly coupled thereto and configured to deliver fluid from a fluid source to the device, or configured to deliver a vacuum from a vacuum source to the device.

4. The system of claim 3, wherein the membrane comprises a dual layer membrane with a channel disposed therebetween, and wherein the channel is fluidly coupled with the fluid delivery or fluid removal tube.

5. The system of claim 1, wherein the first fluid delivery or fluid evacuation device is configured to deliver fluid to the surgical site and configured to evacuate fluid from the surgical site.

6. The system of claim 1, wherein the ring comprises an inner layer of material, an outer layer of material and a support member disposed therebetween, the support member providing support to prevent collapse of the inner and outer layers toward one another.

7. The system of claim 1, wherein the ring comprises an inner layer of material, an outer layer of material and a fluid dispersion member disposed therebetween and configured to distribute the fluid about a perimeter of the ring.

8. The system of claim 1, wherein the first fluid delivery or fluid evacuation device is discrete and releasably coupled with the surgical retractor.

9. The system of claim 1, wherein the first fluid delivery or fluid evacuation device is integrally formed with the surgical retractor.

10. The system of claim 1, wherein the first fluid delivery or fluid evacuation device comprises a permeable outer layer of material fixedly attached to the surgical retractor thereby forming a channel disposed therebetween, and wherein fluid or vacuum is delivered through the channel and through the permeable outer layer of material to the surgical site.

11. The system of claim 10, further comprising an intermediate layer of material disposed in the channel, the intermediate layer of material configured to support the channel and help prevent collapse of the permeable outer layer of material and the surgical retractor toward one another.

12. The system of claim 11, wherein the intermediate layer of material comprises foam.

13. The system of claim 1, wherein the first fluid delivery or fluid evacuation device is a first fluid delivery device, and wherein a fluid is stored in the first fluid delivery device, and wherein the fluid is delivered to the surgical site without requiring fluid coupling between the first fluid delivery device and an external fluid source.

14. The system of claim 13, wherein the fluid is stored in an absorbable material coupled to the first fluid delivery device.

15. The system of claim 1, wherein the first fluid delivery or fluid evacuation device comprises a layer of absorbent material, the layer of absorbent material holding the fluid and configured to deliver the fluid to the surgical site.

16. The system of claim 15, wherein the first fluid delivery or fluid evacuation device comprises a second layer of absorbent material, the second layer of absorbent material positioned to absorb excess fluid from the surgical site.

17. The system of claim 1, wherein the first fluid delivery or fluid evacuation device comprises an inner layer of material and an outer permeable layer of material, and wherein the layers of material are sealed to one another in a quilted pattern.

18. The system of claim 1, wherein the first fluid delivery or fluid evacuation device is a fluid delivery device comprising a gutter for collecting the fluid.

19. The system of claim 1, further comprising a second fluid delivery or fluid evacuation device coupled with the surgical retractor, the second fluid delivery or fluid evacuation device configured to deliver fluid to the surgical site or configured to evacuate fluid from the surgical site.

20. The system of claim 19, wherein the first fluid delivery or fluid evacuation device is a fluid delivery device that delivers a fluid to the surgical site, and wherein the second fluid delivery or fluid evacuation device is a fluid evacuation device that delivers a vacuum to the surgical site to evacuate fluid from the surgical site.

21. The system of claim 19, wherein the second fluid delivery or fluid evacuation device comprises a ring disposed around an outer surface of the surgical retractor.

22. The system of claim 1, further comprising the fluid, and wherein the fluid comprises saline or an antibiotic.

23. The system of claim 1, further comprising an exothermic reagent for generating heat and warming the surgical site.

24. The system of claim 1, further comprising a circulating system for collecting the fluid from the surgical site and redelivering the fluid to the surgical site.

25. The system of claim 1, further comprising a sealing element disposed between a patient's skin and the surgical retractor or the first fluid delivery or fluid evacuation device, the sealing element configured to prevent leakage of the fluid from the surgical site.

26. The system of claim 1, further comprising a surgical access port having a resilient access membrane biased to collapse into a relaxed configuration thereby substantially closing any punctures formed by a hand or a surgical instrument passing through the resilient access membrane.

27. The system of claim 1, further comprising an illumination element for illuminating the surgical site.

28. The system of claim 27, wherein the illumination element provides visible light or ultraviolet light.

29. The system of claim 1, wherein the ring is integrally formed with the membrane.

30. The system of claim 1, wherein the ring completely encircles a circumference of the membrane.

31. The system of claim 1, wherein the ring comprises a plurality of holes disposed therein, the holes allowing fluid or suction to pass therethrough.

32. The system of claim 1, further comprising a fluid source fluidly coupled with the ring.

33. The system of claim 1, wherein the ring is slidably disposed on the membrane.

34. The system of claim 1, comprising both the first fluid delivery and fluid evacuation device.

35. A method for accessing a surgical site through an incision in a patient's body, said method comprising:
providing a surgical retractor and a first fluid delivery or fluid evacuation device, wherein the surgical retractor comprises an upper retention member, a lower retention member and a membrane disposed therebetween, and wherein the first fluid delivery or fluid evacuation device forms a ring coupled to an outer surface of the membrane, the ring having a width d1 and the ring being disposed a distance d2 from the lower retention member, wherein d1 is greater than d2, and wherein d2 is non-zero;
inserting the surgical retractor through the incision;
retracting tissue in the surgical site with the surgical retractor; and
delivering fluid to the surgical site from the first fluid delivery device, or evacuating fluid from the surgical site to the first fluid evacuation device.

36. The method of claim 35, wherein retracting the tissue comprises radially expanding or collapsing an expandable or collapsible upper retention ring coupled to the surgical retractor.

37. The method of claim 35, further comprising coupling a fluid delivery tube or a fluid removal tube to the first fluid delivery or fluid evacuation device, the fluid delivery tube or the fluid removal tube allowing a fluid connection between the first fluid delivery or fluid evacuation device and a source of the fluid, or a source of vacuum.

38. The method of claim 35, wherein the first fluid delivery or fluid evacuation device is a fluid delivery device having a fluid stored therein, and delivering the fluid comprises releasing the stored fluid.

39. The method of claim 38, wherein the fluid is delivered without requiring coupling of the fluid delivery device with an external source of fluid.

40. The method of claim 38, wherein the stored fluid is stored in an absorbent material.

41. The method of claim 35, wherein delivering the fluid comprises delivering saline or an antibiotic to the surgical site.

42. The method of claim 35, wherein the first fluid delivery or fluid evacuation device further comprise an inner layer of material and an outer permeable layer, the method further comprising providing a support element disposed between the inner layer and the outer layer of material, the support element providing support to prevent collapse of the layers inward toward one another.

43. The method of claim 35, further comprising providing a second fluid delivery or fluid evacuation device, the method further comprising:
coupling the second fluid delivery or fluid evacuation device with the surgical retractor;
delivering fluid to the surgical site from the first fluid delivery device; and
evacuating fluid from the surgical site with the second fluid evacuation device.

44. The method of claim 35, further comprising heating the surgical site.

45. The method of claim 35, further comprising illuminating the surgical site with light.

46. The method of claim 45, wherein the illuminating comprises illuminating the surgical site with visible light or ultraviolet light.

47. The method of claim 35, wherein the ring is integrally formed with the membrane.

48. The method of claim 35, wherein the ring completely encircles a circumference of the membrane.

49. The method of claim 35, wherein the ring comprises a plurality of holes disposed therein, the method comprising passing fluid or suction through the plurality of holes.

50. The method of claim 35, further comprising fluidly coupling a fluid source with the ring.

51. The method of claim 35, further comprising slidably disposing the ring on the membrane.

52. The method of claim 35, wherein providing comprises providing both the first fluid delivery and the fluid evacuation device.

* * * * *